US012653477B2

(12) United States Patent
Shiroishi et al.

(10) Patent No.: US 12,653,477 B2
(45) Date of Patent: Jun. 16, 2026

(54) MEDICAL IMAGE PROCESSING DEVICE TO GENERATE A BLOOD VESSEL DIAGRAM SHOWING A BLOOD VESSEL DISTRIBUTION

(71) Applicant: CANON KABUSHIKI KAISHA, Tokyo (JP)

(72) Inventors: Ryo Shiroishi, Nasushiobara (JP); Takuya Sakaguchi, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 229 days.

(21) Appl. No.: 18/485,511

(22) Filed: Oct. 12, 2023

(65) Prior Publication Data

US 2024/0122563 A1     Apr. 18, 2024

(30) Foreign Application Priority Data

Oct. 14, 2022    (JP) ................................. 2022-165867

(51) Int. Cl.
| | |
|---|---|
| *A61B 6/50* | (2024.01) |
| *A61B 6/00* | (2024.01) |
| *A61B 6/46* | (2024.01) |
| *G06T 7/00* | (2017.01) |
| *G16H 30/40* | (2018.01) |

(52) U.S. Cl.
CPC .............. *A61B 6/504* (2013.01); *A61B 6/461* (2013.01); *A61B 6/5223* (2013.01); *G06T 7/0012* (2013.01); *G16H 30/40* (2018.01); *G06T 2207/30101* (2013.01)

(58) Field of Classification Search
CPC ....... A61B 6/504; A61B 6/461; A61B 6/5223; A61B 6/5217; A61B 6/481; A61B 6/032; A61B 5/004; A61B 5/055; A61B 5/72; A61B 6/5211; A61B 2576/02; G06T 7/0012; G06T 2207/30101; G06T 11/003; G16H 30/40
See application file for complete search history.

(56) References Cited

U.S. PATENT DOCUMENTS 9,888,969 B2 * 2/2018 Cohen ..................... A61B 6/504
10,499,871 B2 * 12/2019 Ohishi ................... A61B 6/504
(Continued)

FOREIGN PATENT DOCUMENTS

| JP | 2004-283373 A | 10/2004 |
|---|---|---|
| JP | 2019-193808 A | 11/2019 |
| WO | WO 2014/111927 A1 | 7/2014 |

OTHER PUBLICATIONS

English Machine Translation of CN 114451907 (Sun, Published May 10, 2022) (Year: 2022).*
(Continued)

*Primary Examiner* — Juan M Guillermety
(74) *Attorney, Agent, or Firm* — Oblon, McClelland, Maier & Neustadt, L.L.P.

(57) ABSTRACT

According to an embodiment, a medical image processing device includes processing circuitry. The processing circuitry acquires an angiographic image of a subject. The processing circuitry detects branch points of blood vessels of the subject on the basis of the angiographic image. The processing circuitry generates a blood vessel diagram, which is a diagram showing a blood vessel distribution, on the basis of the branch points.

14 Claims, 20 Drawing Sheets

(56)  References Cited

U.S. PATENT DOCUMENTS

| | | | |
|---|---|---|---|
| 11,633,167 B2 * | 4/2023 | Dascal ................. | G06T 7/0012 |
| | | | 382/132 |
| 2004/0249270 A1 | 12/2004 | Kondo et al. | |
| 2010/0183207 A1 * | 7/2010 | Sakaguchi ............ | A61B 6/507 |
| | | | 382/128 |
| 2018/0214005 A1 * | 8/2018 | Ebata ................... | A61B 5/0205 |
| 2020/0359981 A1 * | 11/2020 | Straka ................... | A61B 5/055 |

OTHER PUBLICATIONS

Schellinger et al., "Noninvasive Angiography (Magnetic Resonance and Computed Tomography) in the Diagnosis of Ischemic Cerebrovascular Disease", Cerebrovasc Dis 2007;24(suppl 1), pp. 16-23.

* cited by examiner

FIG. 6

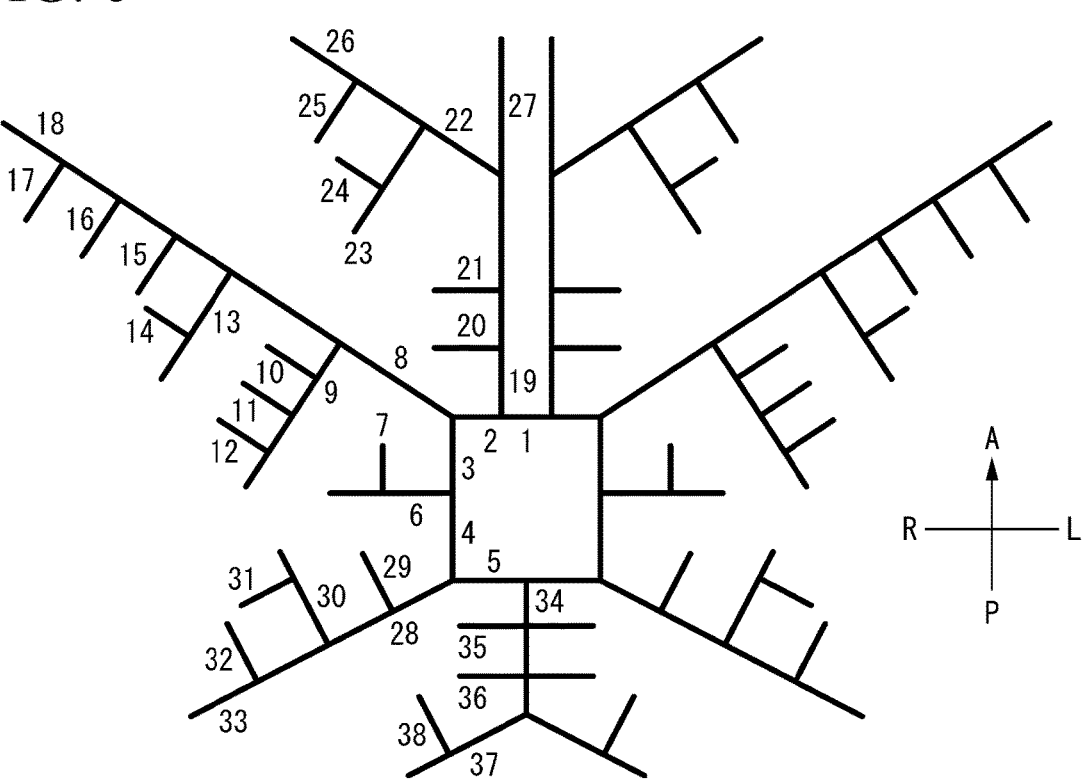

FIG. 7

| | |
|---|---|
| 1. ANTERIOR COMMUNICATING ARTERY | 20. INSIDE ANTERIOR BASILAR ARTERY |
| 2. ANTERIOR CEREBRAL ARTERY A1 | 21. FRONTAL POLAR ARTERY |
| 3. INTERNAL CAROTID ARTERY C1 | 22. CALLOSOMARGINAL ARTERY |
| 4. POSTERIOR COMMUNICATING ARTERY | 23. MIDDLE INTERNAL FRONTAL ARTERY |
| 5. POSTERIOR CEREBRAL ARTERY P1 | 24. ANTERIOR INTERNAL FRONTAL ARTERY |
| 6. INTERNAL CAROTID ARTERY | 25. POSTERIOR INTERNAL FRONTAL ARTERY |
| 7. OPHTHALMIC ARTERY | 26. PARACENTRAL ARTERY |
| 8. MIDDLE CEREBRAL ARTERY | 27. PERICALLOSAL ARTERY |
| 9. CENTRAL SULCUS ARTERY | 28. POSTERIOR CEREBRAL ARTERY |
| 10. OUTSIDE ANTERIOR BASILAR ARTERY | 29. ANTERIOR TEMPORAL ARTERY |
| 11. PREFRONTAL ARTERY | 30. POSTERIOR TEMPORAL ARTERY |
| 12. PRECENTRAL SULCUS ARTERY | 31. POSTERIOR PERIPOLAR ARTERY |
| 13. TEMPORAL POLAR ARTERY | 32. CALCARINE ARTERY |
| 14. ANTERIOR TEMPORAL ARTERY | 33. POSTERIOR PARIETAL ARTERY |
| 15. ANTERIOR PARIETAL ARTERY | 34. BASILAR ARTERY |
| 16. POSTERIOR PARIETAL ARTERY | 35. SUPERIOR CEREBELLAR ARTERY |
| 17. POSTERIOR TEMPORAL ARTERY | 36. ANTERIOR INFERIOR CEREBELLAR ARTERY |
| 18. ANGULAR ARTERY | 37. CAROTID ARTERY |
| 19. ANTERIOR CEREBRAL ARTERY | 38. POSTERIOR INFERIOR CEREBELLAR ARTERY |

FIG. 15
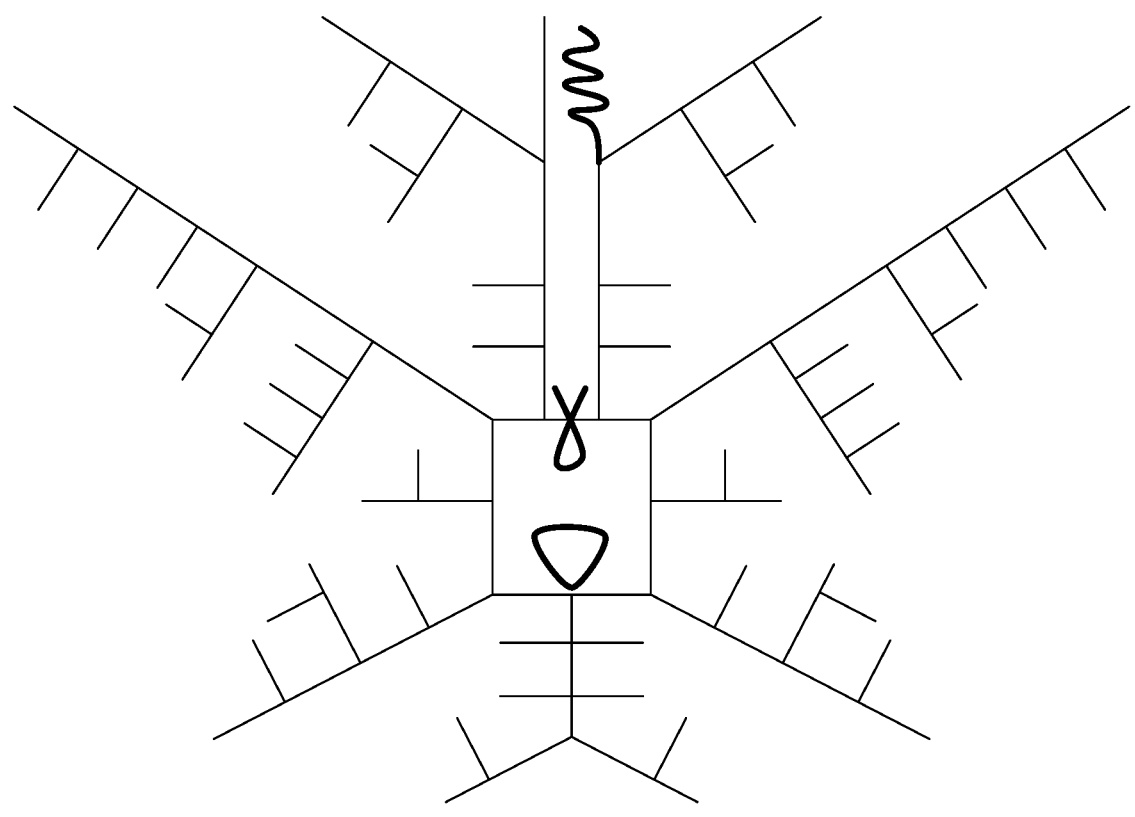
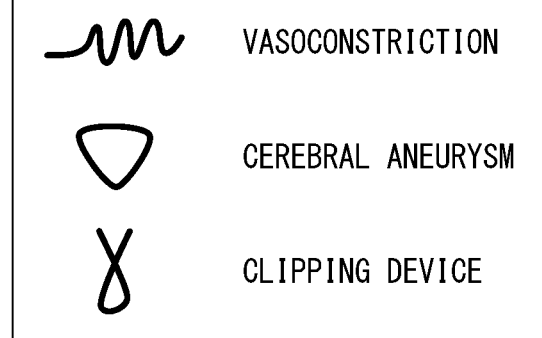

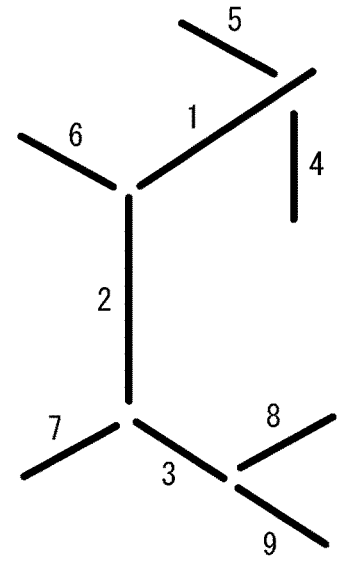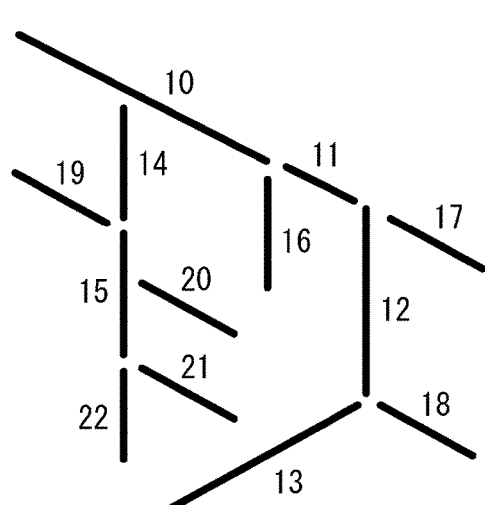

FIG. 24

| RIGHT CORONARY ARTERY | LEFT CORONARY ARTERY |
|---|---|
| 1. RIGHT CORONARY ARTERY 1 | 10. ANTERIOR DESCENDING BRANCH 1 |
| 2. RIGHT CORONARY ARTERY 2 | 11. ANTERIOR DESCENDING BRANCH 2 |
| 3. RIGHT CORONARY ARTERY 3 | 12. ANTERIOR DESCENDING BRANCH 3 |
| 4. SINUS NODE BRANCH | 13. ANTERIOR DESCENDING BRANCH 4 |
| 5. CONUS BRANCH | 14. CIRCUMFLEX BRANCH 1 |
| 6. RIGHT VENTRICULAR BRANCH | 15. CIRCUMFLEX BRANCH 2 |
| 7. ACUTE MARGINAL BRANCH | 16. SEPTAL BRANCH |
| 8. ATRIOVENTRICULAR BRANCH | 17. FIRST DIAGONAL BRANCH |
| 9. POSTERIOR DESCENDING BRANCH | 18. SECOND DIAGONAL BRANCH |
| | 19. ATRIOVENTRICULAR NODE BRANCH |
| | 20. OBTUSE MARGINAL BRANCH |
| | 21. POSTEROLATERAL BRANCH |
| | 22. POSTERIOR DESCENDING BRANCH |

MEDICAL IMAGE PROCESSING DEVICE TO GENERATE A BLOOD VESSEL DIAGRAM SHOWING A BLOOD VESSEL DISTRIBUTION

CROSS-REFERENCE TO RELATED APPLICATION

Priority is claimed on Japanese Patent Application No. 2022-165867, filed Oct. 14, 2022, the content of which is incorporated herein by reference.

FIELD

Embodiments disclosed herein and drawings relate to a medical image processing device, a medical image processing method, and a storage medium.

BACKGROUND

Although a standard shape or blood flow is known for a cerebral blood vessel, a subject may have a shape or a blood flow different from a standard according to individual differences and diseases of the subject. In the diagnosis of cerebral blood vessel areas, it is important for physicians to ascertain a shape of a cerebral blood vessel or a blood flow specific to the subject for identification of the cause of a disease and decision of treatment strategies.

Conventionally, the shape or blood flow of a cerebral blood vessel is ascertained using a 3D medical image of a head imaged by a modality such as an X-ray computed tomography (CT) device or a magnetic resonance imaging (MRI) device. The 3D medical image of the head is a 3D image in which 2D images (slices) at a plurality of cross-sectional positions are collected.

In CT, a contrast medium is intravenously injected into the subject and head contrast CT imaging is performed to obtain a CT angiography (CTA) image. Because the CTA image has a high X-ray absorption coefficient of the contrast medium, it is an image shown with a large pixel value in the blood vessel into which the contrast medium flows. If CT imaging is performed continuously in time according to the injection of the contrast medium, a multi-time-phase 4D-CTA image showing the state of the inflow of the contrast medium can also be obtained.

Likewise, in MRI, MR angiography (MRA) images using a contrast medium are obtained. If the incoming blood is labeled magnetically in advance, a non-contrast MRA image without using a contrast medium can also be obtained. If MRI imaging is performed continuously in time, a multi-time-phase 4D-MRA image can also be obtained in a contrast or non-contrast mode.

Physicians visually observe and ascertain the shape of a blood vessel using CTA and MRA images. To confirm the shape of a blood vessel with CTA and MRA images, a physician needs to confirm a large number of images (slices) in order to avoid missing abnormalities such as slight blood vessel defects. This process is time-consuming.

Also, a physician visually observes and ascertains the state of a blood flow using 4D-CTA and 4D-MRA images. To confirm a blood flow is confirmed with 4D-CTA or 4D-MRA images, a physician needs to confirm images of all time phases to avoid missing even the slightest interruption or regurgitation of a blood flow. This process is also time-consuming.

In this way, in conventional technology, a process of confirming the shape and the blood flow of a cerebral blood vessel is time-consuming. These problems are not limited to the brain, but are common to blood vessels in other portions of the body (for example, the heart, lungs, liver, kidneys, small intestine, and the like).

BRIEF DESCRIPTION OF THE DRAWINGS

FIG. 6 is an example of a standard blood vessel diagram of a cerebral artery.

FIG. 7 is a list of names of arteries drawn as a standard blood vessel diagram of cerebral arteries.

FIG. 15 is an example of a blood vessel diagram according to the third embodiment.

FIG. 23 is an example of a standard blood vessel diagram of a coronary artery.

FIG. 24 is a list of names of arteries drawn as a standard blood vessel diagram of the coronary arteries.

FIG. 25 is an example of a blood vessel diagram according to the fifth embodiment.

DETAILED DESCRIPTION

Hereinafter, a medical image processing device, a medical image processing method, and a storage medium of embodiments will be described with reference to the drawings. According to an embodiment, the medical image processing device includes processing circuitry. The processing circuitry acquires an angiographic image of a subject. The processing circuitry detects branch points of blood vessels of the subject on the basis of the angiographic image. The processing circuitry generates a blood vessel diagram, which is a diagram showing a blood vessel distribution, on the basis of the branch points. By providing a user with the blood vessel diagram generated in this way, the user can ascertain a shape or a blood flow of a blood vessel in a shorter period of time.

First Embodiment

[Configuration of Medical Image Processing Device]

Figure 1:
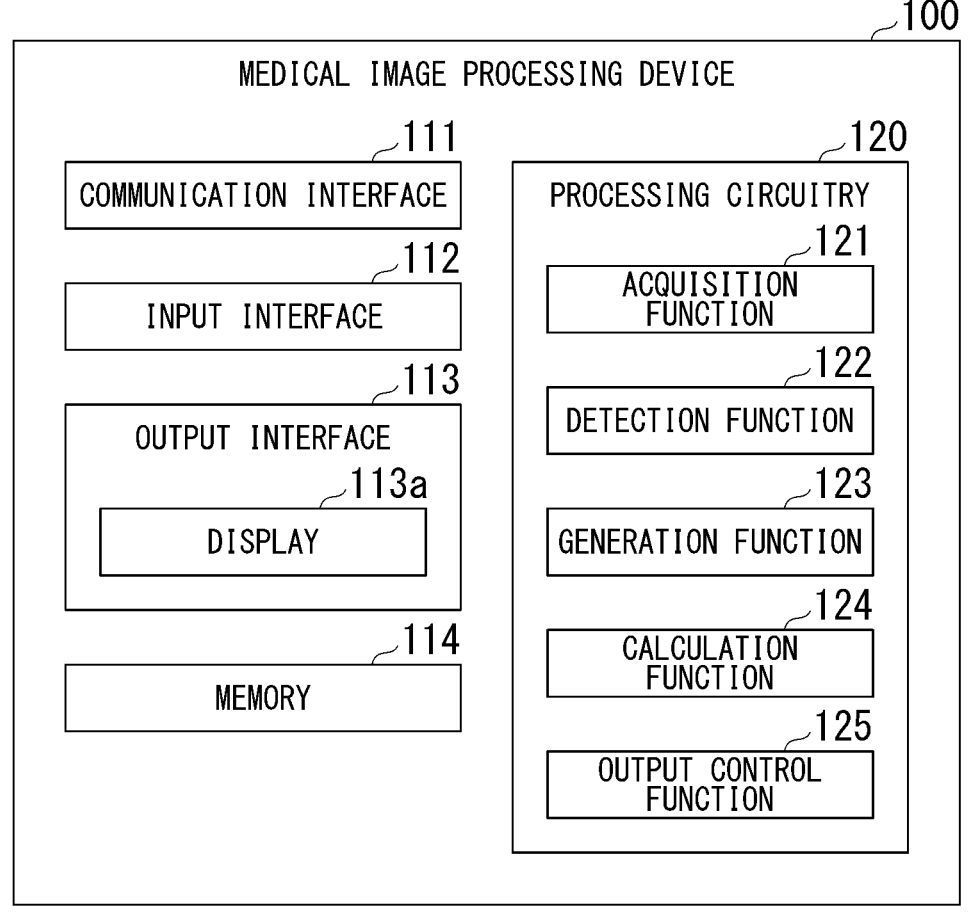
FIG. 1 is a diagram showing an example of a configuration of a medical image processing device in a first embodiment.

FIG. 1 is a diagram showing an example of a configuration of a medical image processing device 100 in a first embodiment. The medical image processing device 100 includes, for example, a communication interface 111, an input interface 112, an output interface 113, a memory 114, and processing circuitry 120.

The medical image processing device 100 may be a single device or a system in which a plurality of devices connected via a communication network NW operate in cooperation with each other. That is, the medical image processing device 100 may be implemented by a plurality of computers (processors) included in a distributed computing system or a cloud computing system.

The communication interface 111 communicates with a medical image diagnostic device or the like via the communication network NW. The communication interface 111 includes, for example, a network interface card (NIC), an antenna for wireless communication, and the like.

The communication network NW may be a general information and communication network using telecommunication technology. For example, the communication network NW includes a telephone communication circuit network, an optical fiber communication network, a cable communication network, a satellite communication network, and the like as well as a wireless/wired local area network (LAN) such as a hospital-backbone LAN or an Internet network.

The medical image diagnostic device is a modality such as an X-ray computed tomography (CT) device or a magnetic resonance imaging (MRI) device.

The input interface 112 receives various types of input operations from an operator, converts the received input operations into electrical signals, and outputs the electrical signals to the processing circuitry 120. For example, the input interface 112 includes a mouse, a keyboard, a trackball, a switch, a button, a joystick, a touch panel, and the like. The input interface 112 may be, for example, a user interface that receives a sound input such as a microphone. When the input interface 112 is a touch panel, the input interface 112 may have a display function of a display 113*a* included in the output interface 113 to be described below.

Also, in the present specification, the input interface 112 is not limited to one including physical operation components such as a mouse and a keyboard. For example, electrical signal processing circuitry configured to receive an electrical signal corresponding to an input operation from external input equipment provided separately from the device and output this electrical signal to a control circuit is also included as an example of the input interface 112.

The output interface 113 includes, for example, the display 113*a*, a speaker 113*b*, and the like.

The display 113*a* displays various types of information. For example, the display 113*a* displays an image generated by the processing circuitry 120, a graphical user interface (GUI) for receiving various types of input operations from the operator, and the like. For example, the display 113*a* is a liquid crystal display (LCD), a cathode ray tube (CRT) display, an organic electro luminescence (EL) display, or the like.

The speaker 113*b* outputs information input from the processing circuitry 120 as a sound.

The memory 114 is implemented by a semiconductor memory element such as a random-access memory (RAM) or a flash memory, a hard disk, or an optical disc. These non-transitory storage media may be implemented by other storage devices connected via the communication network NW such as a network attached storage (NAS) or an external storage server device. Also, the memory 114 may include a non-transitory storage medium such as a read-only memory (ROM) or a register. The memory 114 is an example of a "storage unit."

The processing circuitry 120 includes, for example, an acquisition function 121, a detection function 122, a generation function 123, a calculation function 124, and an output control function 125. The acquisition function 121 is an example of an "acquisition unit," the detection function 122 is an example of a "detection unit," the generation function 123 is an example of a "generation unit," the calculation function 124 is an example of a "calculation unit," and the output control function 125 is an example of a "display control unit."

In the processing circuitry 120, for example, a hardware processor (a computer) executes a program stored in the memory 114 (storage circuitry) to implement these functions.

The hardware processor in the processing circuitry 120 is, for example, circuitry such as a central processing unit (CPU), a graphics processing unit (GPU), an application-specific integrated circuit (ASIC), or a programmable logic device (for example, a simple programmable logic device (SPLD), a composite programmable logic device (CPLD), or a field programmable gate array (FPGA)). Instead of storing the program in the memory 114, the program may be directly incorporated in the circuitry of the hardware processor. In this case, the hardware processor reads and executes a program incorporated in the circuitry to implement the function. The program may be previously stored in the memory 114 or stored in a non-transitory storage medium such as a DVD or a CD-ROM, and installed in the memory 114 from the non-transitory storage medium when the non-transitory storage medium is loaded in a drive device (not shown) of the medical image processing device 100. The hardware processor is not limited to the configuration of single circuitry and may be configured as a single hardware processor by combining a plurality of pieces of independent circuitry to implement each function. Also, a plurality of components may be integrated into one hardware processor to implement each function.

[Processing Flow of Medical Image Processing Device]

Figure 2:
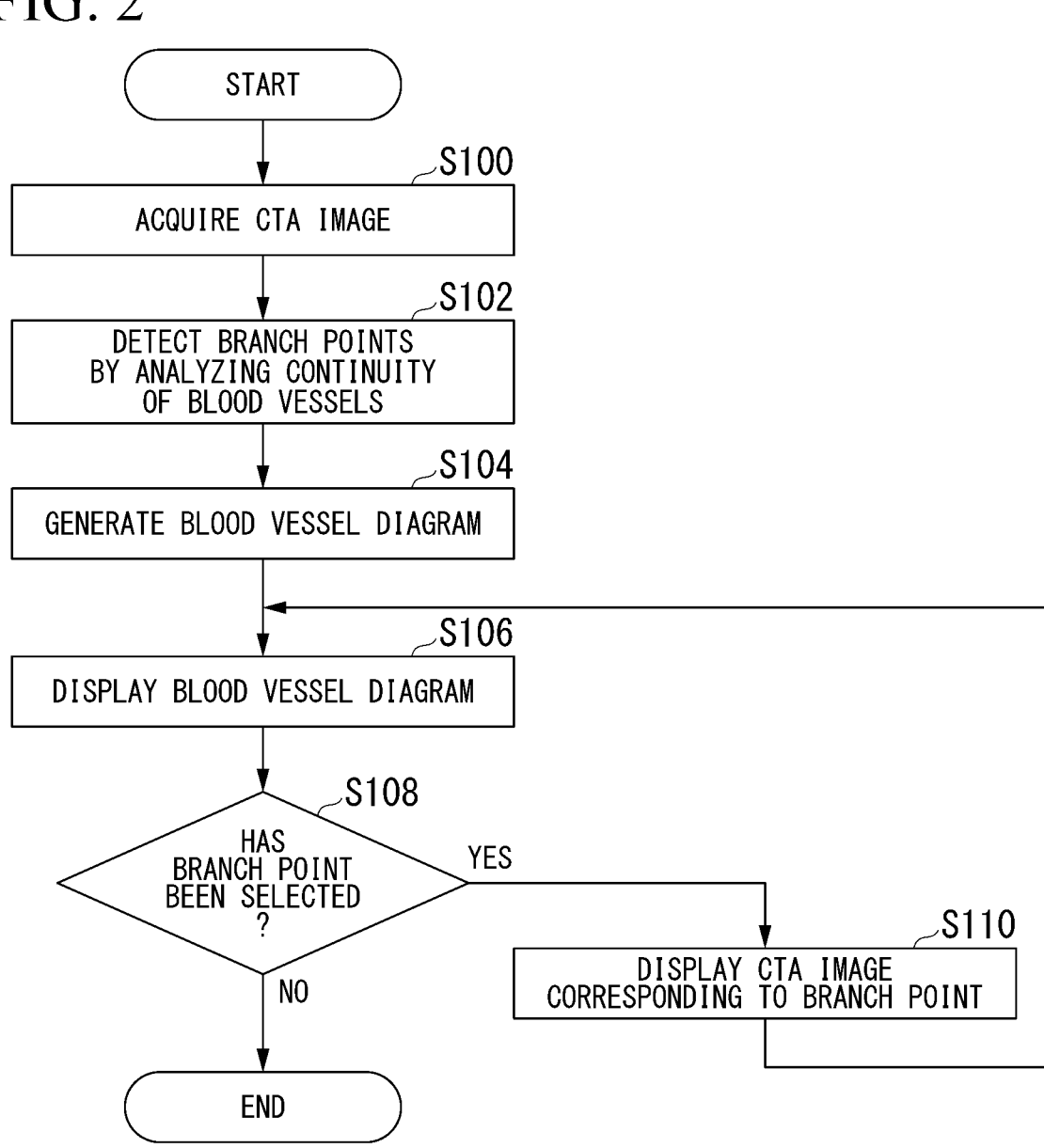
FIG. 2 is a flowchart showing a flow of a series of processing steps of processing circuitry according to the first embodiment.

Hereinafter, a series of processing steps of the processing circuitry 120 of the medical image processing device 100 will be described with reference to the flowchart. FIG. 2 is a flowchart showing a flow of the series of processing steps of the processing circuitry 120 according to the first embodiment. In the present flowchart, as an example, a medical image diagnostic device is referred to as an X-ray CT device and a medical image is referred to as a CTA image.

First, the acquisition function 121, for example, is performed to acquire a CTA image IMG1 from the X-ray CT device via the communication interface 111 (step S100). When the CTA image IMG1 is stored in the memory 114, the acquisition function 121 may acquire the CTA image IMG1 from the memory 114.

The CTA image IMG1 is a CT image obtained by the X-ray CT device imaging a portion of a subject into whom a contrast medium has been injected. Typically, the CTA image IMG1 is a three-dimensional CT image (3D-CTA image) in which cross-sectional images of a portion of the subject into whom a contrast medium is injected are connected (associated) when the portion is imaged from a plurality of positions different from each other. The CTA image IMG1 is not limited to the 3D-CTA image, but may be a multi-time-phase 4D-CTA image. When the CTA image IMG1 is a multi-time-phase 4D-CTA image, the acquisition function 121 may be performed to perform a time-specific maximum intensity projection (MIP) process to convert the 4D-CTA image into a 3D-CTA image. Hereinafter, the portion of the subject imaged by the X-ray CT device will be described as being a "brain." The CTA image is an example of an "angiographic image."

Subsequently, the detection function 122 is performed to analyze the continuity of the blood vessels in the brain on the basis of the CTA image IMG1 and detect branch points B of the blood vessels on the basis of an analysis result (step S102). The blood vessel serving as an analysis target is typically an "artery," but may not be limited to this and may be a "vein." Hereinafter, as an example, it is assumed that the blood vessel serving as the analysis target is an "artery."

When the detection function 122 detects the branch points B of the artery, the detection function 122 generates a list in which a connection between the branch points B is represented in a data structure (hereinafter referred to as an arterial branch point list LT).

Figure 3:
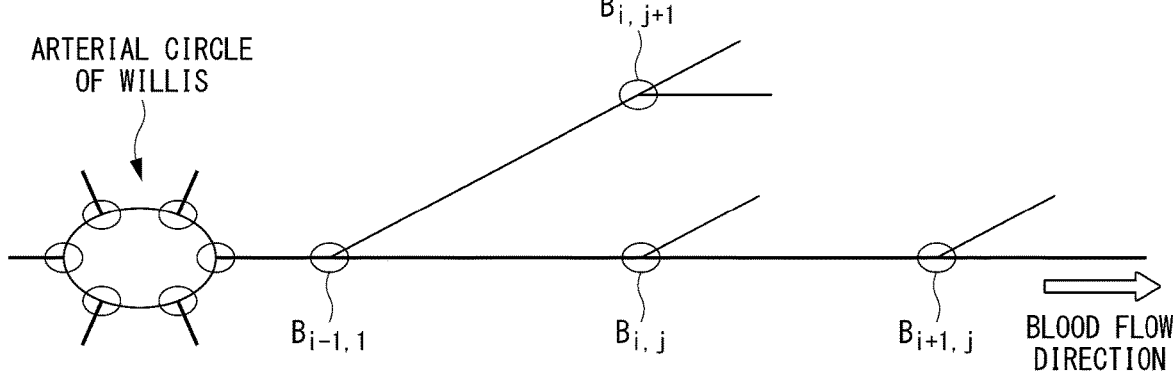
FIG. 3 is a diagram showing an example of an abstracted cerebral artery.
Figure 4:
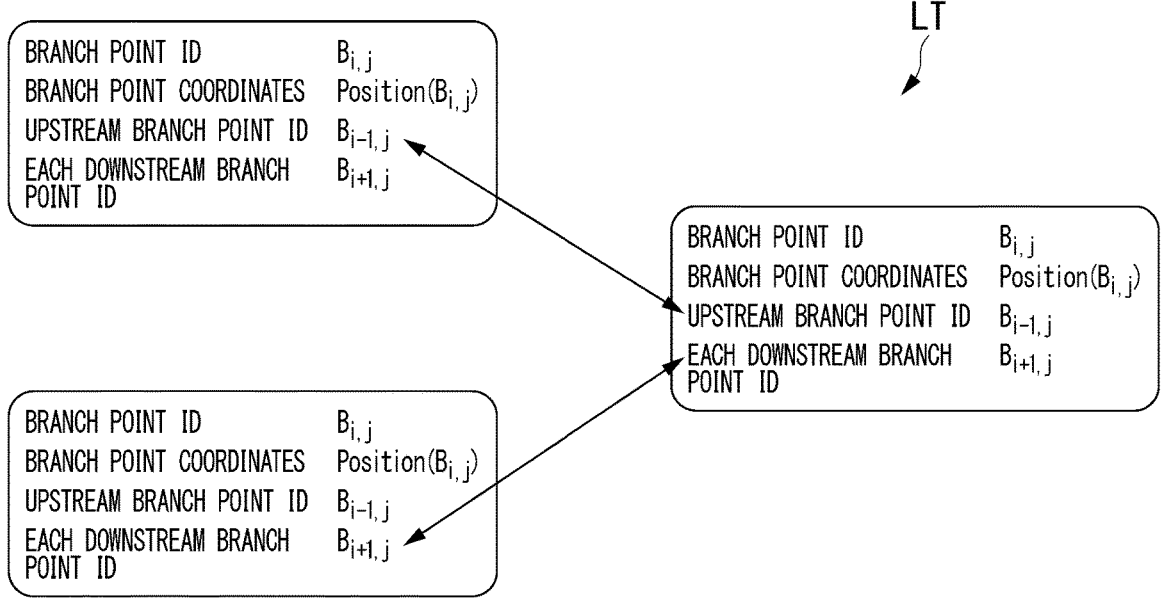
FIG. 4 is a diagram showing an example of an arterial branch point list.
Figure 5:
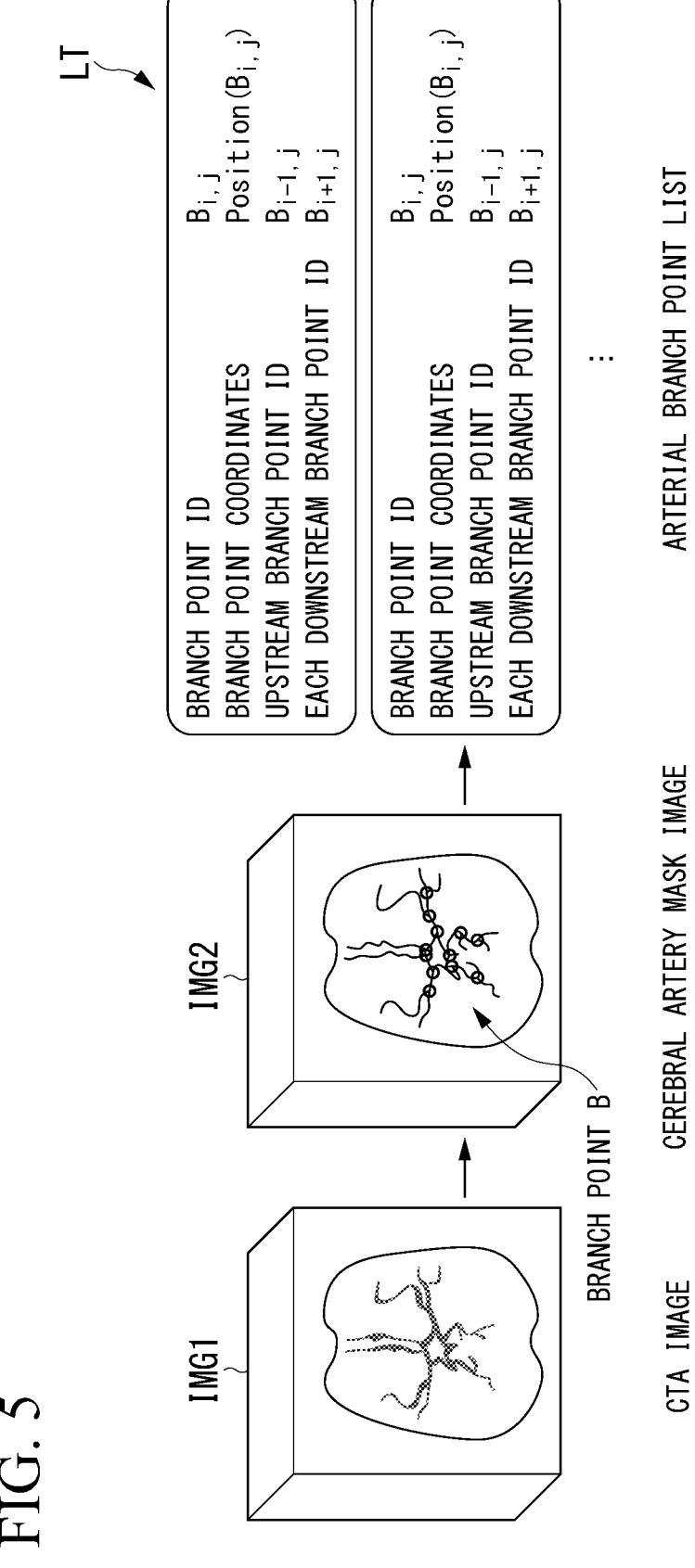
FIG. 5 is a diagram schematically showing a series of flows until the arterial branch point list is generated from a CTA image of the brain.

FIG. 3 is a diagram showing an example of an abstracted cerebral artery, FIG. 4 is a diagram showing an example of the arterial branch point list LT, and FIG. 5 is a diagram schematically showing a series of flows until the arterial branch point list LT is generated from the CTA image IMG1 of the brain.

It is known that the cerebral arteries have a structure that branches from six cerebral arteries toward the periphery (downstream) like the arterial circle of Willis. Therefore, the blood vessels branching from the cerebral artery toward the periphery are considered abstractly as shown in FIG. 3. Specifically, the branch point B where the artery branches may be a node and the cerebral artery may be abstracted by a graph obtained by connecting the nodes with edges.

As shown in FIG. 4, the arterial branch point list LT has information about a branch point ID, branch point coordinates, an upstream branch point ID, and a downstream branch point ID for each branch point and has information about connections with upstream and downstream branch points. For example, when attention is paid to branch points $B_{i,j}$, branch points $B_{i-1,1}$ are located on the upstream side of the branch points $B_{i,j}$, and branch points $B_{i+1,j}$ are located on the downstream side thereof. Thus, a branch point with an ID of "$B_{i,j}$" has "$B_{i-1,1}$" in the upstream branch point ID and "$B_{i+1,j}$" in the downstream branch point ID.

As shown in FIG. 5, the detection function 122 is performed to generate a cerebral artery mask image IMG2, which is an image in which only the cerebral artery is extracted, on the basis of the CTA image IMG1. The cerebral artery mask image IMG2 may be generated, for example, by replacing a pixel having a CT value (a luminance value) greater than or equal to a threshold value with 1 on the CTA image IMG1 and replacing a pixel having a CT value less than the threshold value with 0 using a contrast intensity difference between the artery and others.

The detection function 122 is performed to detect the branch point B of the artery by analyzing the structure of the blood vessel on the cerebral artery mask image IMG2. The artery shown in the cerebral artery mask image IMG2 can have a tubular structure having a thickness in a three-dimensional image and can have a linear structure without thickness in, for example, a three-dimensional thinning process.

The detection function 122 may be performed to scan pixel values of a 3×3×3 cube region along a line from an end of the line on the lower side (cervical side) and detect points where four or more pixels of the cube region have values as the branch points B. The detection function 122 is performed to assign a number to each branch point B, set the number as a branch point ID, and set a position in an image space as branch point coordinates. Also, the detection function 122 sets numbers of adjacent branch points B on the upstream side and the downstream side for each branch point B as an upstream branch point ID and a downstream branch point ID. Also, the detection function 122 is performed to store these in a linked list and generate an arterial branch point list LT.

The description returns to the flowchart of FIG. 2. Subsequently, the generation function 123 generates a blood vessel diagram of the cerebral artery on the basis of the arterial branch point list LT (step S104). The blood vessel diagram of the cerebral artery is a diagram for visualizing a distribution structure of cerebral arteries and the shape and blood flow of the cerebral artery are represented as a diagram.

For example, the generation function 123 may be performed to change (correct) a standard blood vessel diagram (a template blood vessel diagram), which is a diagram for visualizing a standard distribution structure of cerebral arteries to match a connection relationship between two or more branch points B included in the arterial branch point list LT, and generate the changed standard blood vessel diagram as the blood vessel diagram. The standard blood vessel diagram, for example, may be previously stored in the memory 114 or may be downloaded from an external server.

FIG. 6 is an example of a standard blood vessel diagram of cerebral arteries and FIG. 7 is a list of names of arteries drawn as a standard blood vessel diagram of cerebral arteries. For example, the generation function 123 is performed to associate a standard blood vessel diagram with a branch point B included in the arterial branch point list LT at a branch of an upstream blood vessel of the head. Furthermore, the generation function 123 is performed to associate the branches of a left internal carotid artery and an ophthalmic artery of the standard blood vessel diagram with branch point coordinates located on a lowest left anterior side (a cervical side, a left side, and an anterior side) that does not have an upstream branch point in the arterial branch point list LT. Likewise, the generation function 123 is performed to associate the branches of a right internal carotid artery and an ophthalmic artery of the standard blood vessel diagram with branch point coordinates located on a lowest right anterior side (a cervical side, a right side, and an anterior side) that does not have an upstream branch point in the arterial branch point list LT.

Also, the generation function 123 is performed to associate the branches of a left vertebral artery and a posterior inferior cerebellar artery of the standard blood vessel diagram with branch point coordinates located on a lowest left posterior side (a cervical side, a left side, and a posterior side) that does not have an upstream branch point in the arterial branch point list LT. Likewise, the generation function 123 is performed to associate the branches of a right vertebral artery and a posterior inferior cerebellar artery of the standard blood vessel diagram with branch point coordinates located on a lowest right posterior side (a cervical side, a right side, and a posterior side) that does not have an upstream branch point in the arterial branch point list LT. The generation function 123 is performed to trace the connection with the downstream branch point in the arterial branch point list LT from the mutually associated branch points. The generation function 123 is performed to represent the artery by a solid line on the blood vessel diagram if the connection can be traced and represent the artery by a dashed line in the blood vessel diagram if the connection cannot be traced.

In place of or in addition to generating a blood vessel diagram using the standard blood vessel diagram and the arterial branch point list LT, the generation function 123 may be performed to generate the blood vessel diagram using only the arterial branch point list LT without using the standard blood vessel diagram. For example, the generation function 123 may be performed to generate a graph in which the branch point B is a node and the blood vessels connecting the branch points B are edges as a blood vessel diagram of cerebral arteries, as shown in FIG. 3, using the arterial branch point list LT. At this time, the generation function 123 may be performed to generate the graph by applying a directed graph optimization method to reduce the number of edge intersections.

The description returns to the flowchart in FIG. 2. Subsequently, the output control function 125 is performed to cause a display 113a of an output interface 113 to display the blood vessel diagram (step S106). Also, in addition to or in place of causing the display 113a to display the blood vessel diagram, the output control function 125 may be performed to transmit the blood vessel diagram to an external display device via the communication interface 111.

Figure 8:
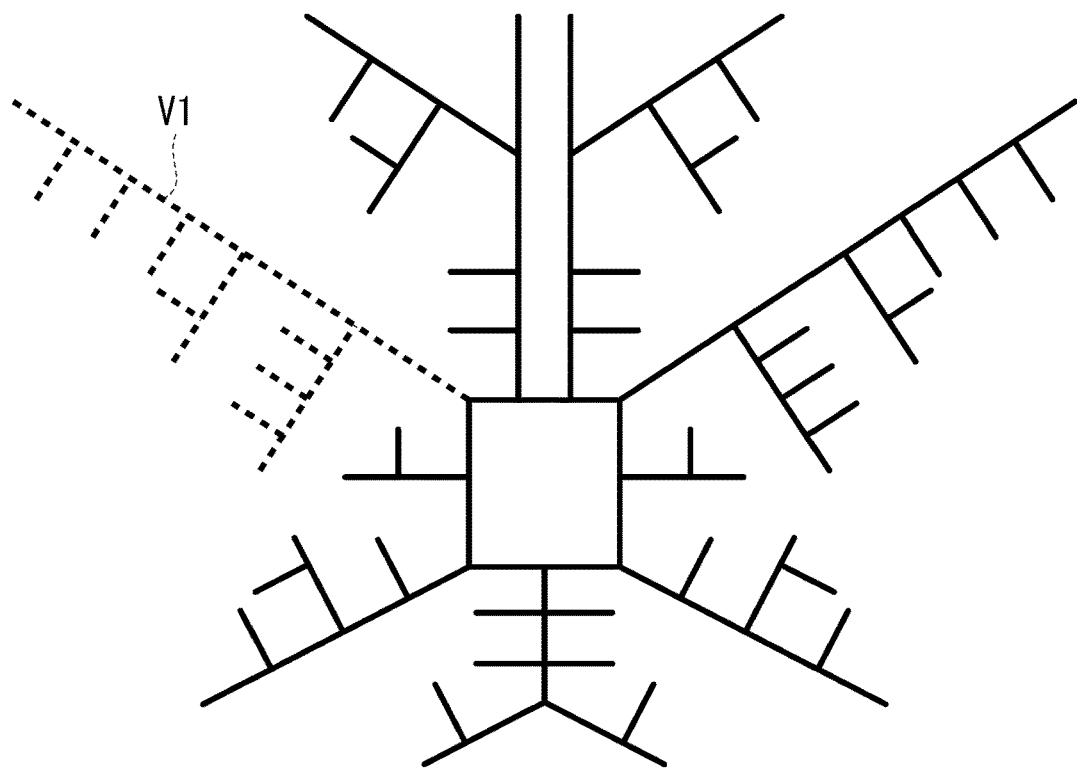
FIG. 8 is an example of a blood vessel diagram according to the first embodiment.
Figure 9:
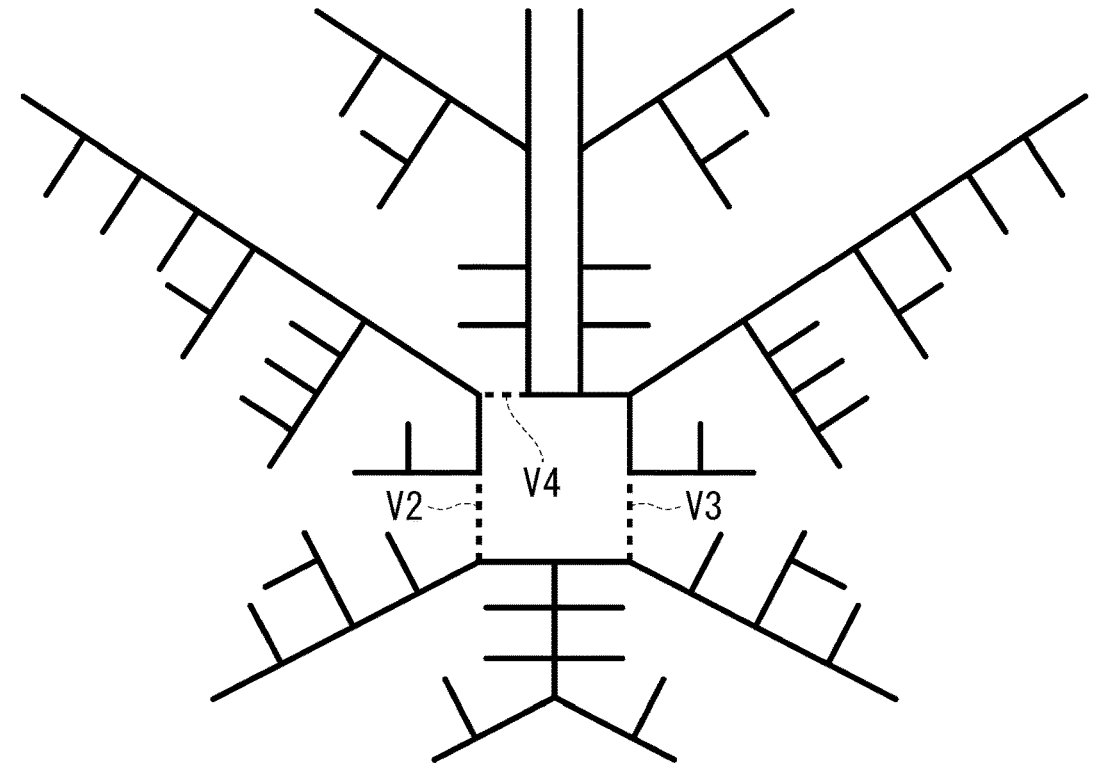
FIG. 9 is another example of the blood vessel diagram according to the first embodiment.

FIGS. 8 and 9 are examples of blood vessel diagrams according to the first embodiment. In the blood vessel diagram of FIG. 8, an artery V1 is represented by a dashed line. That is, the blood vessel diagram of FIG. 8 does not trace a middle cerebral artery (an artery having No. 8) and blood vessels downstream from the middle cerebral artery. In the blood vessel diagram of FIG. 9, arteries V2 to V4 are represented by dashed lines. That is, the blood vessel diagram of FIG. 9 does not trace an anterior cerebral artery A1 and a posterior communicating artery (arteries having Nos. 2 and 4). By displaying such blood vessel diagrams on the display 113a, the physician can ascertain that the right middle cerebral artery is occluded in the case of the blood vessel diagram of FIG. 8 and the anterior cerebral artery A1 and the posterior communicating artery are underdeveloped in the case of the blood vessel diagram of FIG. 9.

The description returns to the flowchart in FIG. 2. Subsequently, after the display 113a is allowed to display the blood vessel diagram, the output control function 125 is performed to determine whether at least one or more branch points B have been selected from among the branch points B of the arterial branch point list LT associated with branches on the blood vessel diagram when the physician (an example of a "user") operates the input interface 112 (step S108). For example, when the input interface 112 is a touch panel that includes the display function of the display 113a, the physician can select the branch point B on the touch panel on which the blood vessel diagram is displayed.

For example, when the physician selects the branch point B, the output control function 125 is performed to select a cross-sectional image in which the selected branch point B is drawn from among a plurality of cross-sectional images (2D-CTA images) constituting the CTA image IMG1, which is a 3D-CTA image, and causes the display 113a to display the cross-sectional image (step S110).

Figure 10:
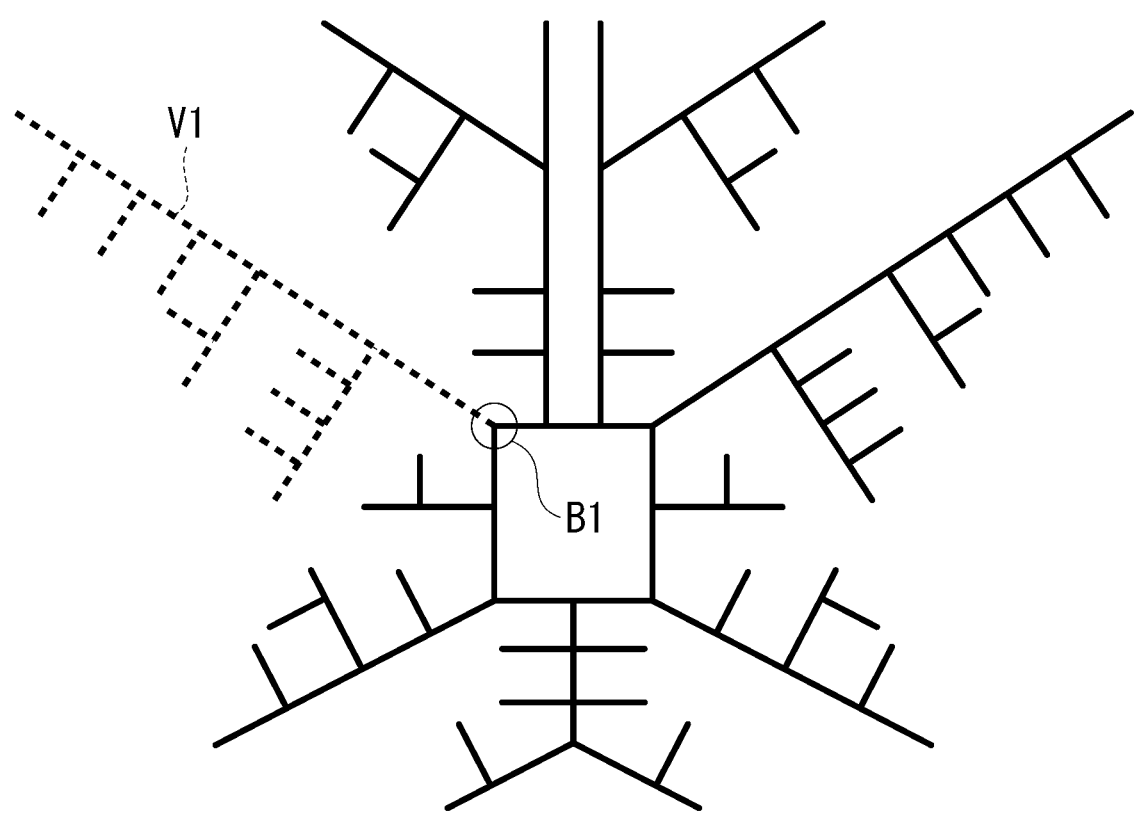
FIG. 10 schematically shows a state in which a branch point is selected on the blood vessel diagram.
Figure 11:
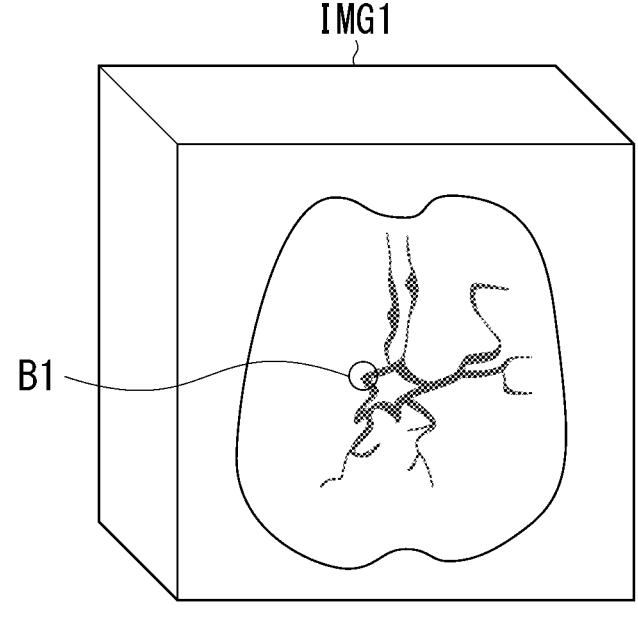
FIG. 11 is a diagram showing an example of a cross-sectional image corresponding to the selected branch point.

FIG. 10 is a diagram schematically showing a state in which a branch point is selected on a blood vessel diagram and FIG. 11 is a diagram showing an example of a cross-sectional image corresponding to the selected branch point. In FIG. 10, a branch point B1 on the upstream side of the artery V1 where the occlusion has occurred is selected. In this case, as shown in FIG. 11, the output control function 125 is performed to select the cross-sectional image in which the branch point B1 is drawn from among a plurality of cross-sectional images constituting the CTA image IMG1 and causes the display 113a to display the cross-sectional image(s).

Also, the edge between the branch points B, i.e., the blood vessel, as well as the branch point B can be selected. For example, when the physician selects a blood vessel between the branch points B, the output control function 125 is performed to identify the branch points B located at both ends of the selected blood vessel and to cause the display 113a to display a cross-sectional image in which the branch points B at both ends of the blood vessel are drawn (a cross-sectional image corresponding to coordinates between the branch points B at both ends of the blood vessel).

The description returns to the flowchart in FIG. 2. When the physician does not select the branch point B or the blood vessel after the display 113a is allowed to display the blood vessel diagram, the process of the present flowchart ends.

According to the above-described first embodiment, the processing circuitry 120 acquires a CTA image IMG1, which is a CT image of the head of the subject into whom the contrast medium has been intravenously injected. The processing circuitry 120 generates a cerebral artery mask image IMG2 on the basis of the CTA image IMG1 and further detects branch points B of the cerebral arteries on the cerebral artery mask image IMG2. The processing circuitry 120 generates a blood vessel diagram of the cerebral arteries on the basis of the arterial branch point list LT in which the connection between the branch points B is represented in a data structure. Also, the processing circuitry 120 causes the display 113a to display the blood vessel diagram. Thus, by schematically displaying the cerebral artery as the blood vessel diagram, the user (typically, the physician) can ascertain the shape or blood flow of the cerebral artery of the subject in a shorter period of time.

Further, according to the above-described first embodiment, when the user has selected a branch point B or a blood vessel between the branch points B on the blood vessel diagram, the processing circuitry 120 selects a cross-sectional image including a branch point B or a blood vessel selected by the user from among a plurality of cross-sectional images (2D-CTA images) constituting the CTA image IMG1, which is a 3D-CTA image, and causes the display 113a to display the cross-sectional image. Thereby, a part of interest of the user on the blood vessel diagram can also be confirmed on the 3D-CTA image.

Modified Examples of First Embodiment

Hereinafter, modified examples of the first embodiment will be described. Although a case where the medical image processing device 100 acquires a CTA image from an X-ray CT device and generates a blood vessel diagram on the basis of the CTA image has been described in the above-described first embodiment, the present invention is not limited thereto. For example, the medical image processing device 100 may acquire an MRA image from the MR device and generate a blood vessel diagram on the basis of the MRA image. Like the CTA image, the MRA image is typically a three-dimensional MR image (3D-MRA image). The MRA image is not limited to 3D-MRA images, but may be a multi-time-phase 4D-MRA image. When the MRA image is a multi-time-phase 4D-MRA image, the medical image processing device 100 may perform a time-specific MIP process to convert the 4D-MRA image into a 3D-MRA image.

Although a case where a portion of the subject (i.e., a portion from which the blood vessel diagram is generated) imaged by the medical image diagnostic device such as the X-ray CT device or the MR device is the "brain" has been described in the above-described first embodiment, the present invention is not limited thereto. For example, the portion of the subject imaged by the medical image diagnostic device may be other portions such as the heart, lungs, liver, kidney, and small intestine. Also, as described above, the blood vessel represented as the blood vessel diagram is not limited to an "artery" but may be a "vein."

Second Embodiment

Hereinafter, a second embodiment will be described. The second embodiment is different from the above-described first embodiment in that a thickness of a blood vessel (a blood vessel diameter) is detected and a blood vessel diagram representing the thickness of the blood vessel is generated. Hereinafter, differences from the first embodiment will be mainly described and content identical to that of the first embodiment will be omitted. Also, in the description of the second embodiment, parts identical to those of the first embodiment are denoted by the same reference signs.

Figure 12:
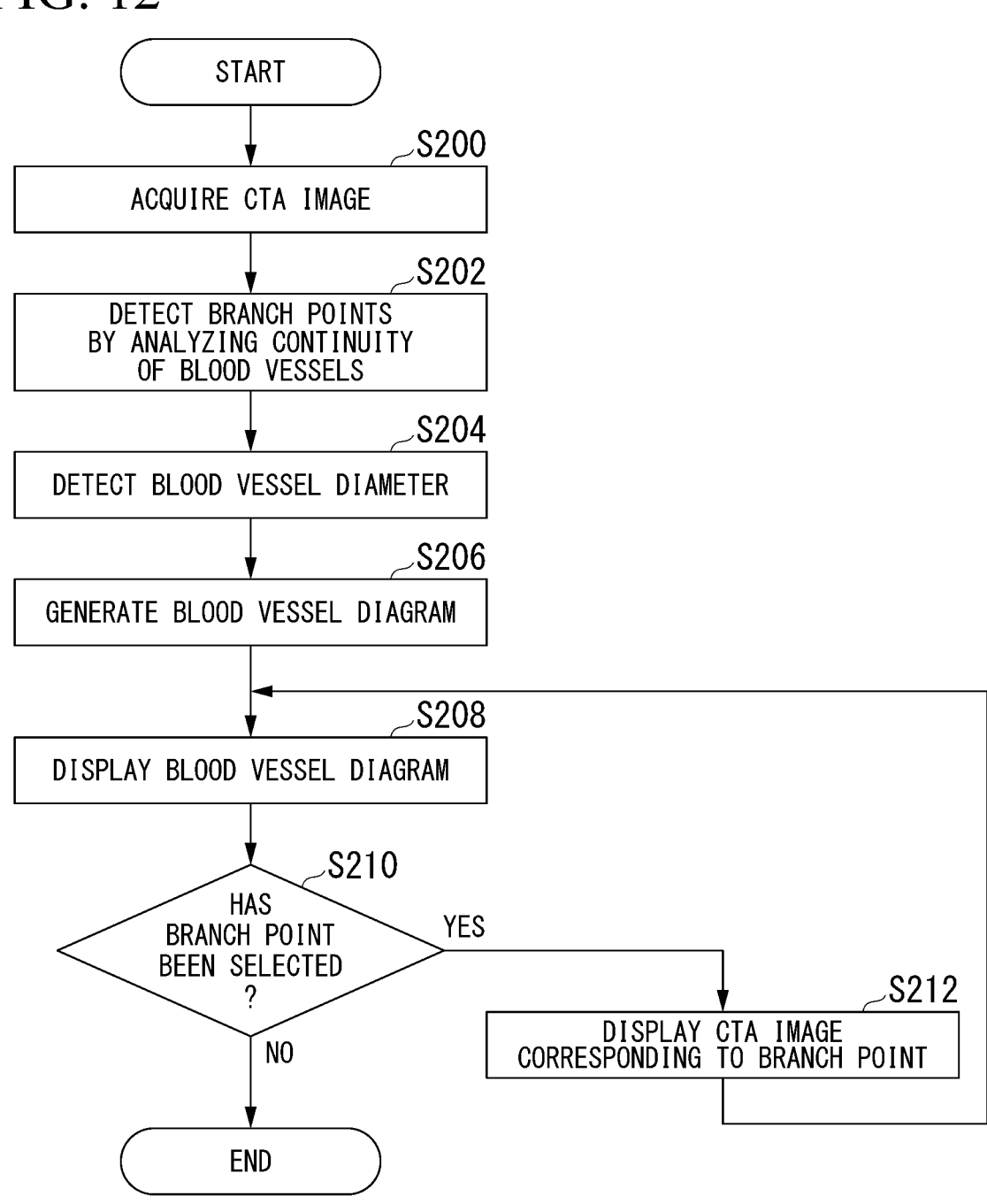
FIG. 12 is a flowchart showing a flow of a series of processing steps of processing circuitry according to a second embodiment.

FIG. 12 is a flowchart showing a flow of a series of processing steps of processing circuitry 120 according to the second embodiment. In the present flowchart, as an example, it is assumed that a medical image diagnostic device is an X-ray CT device and a medical image is a CTA image.

First, an acquisition function 121, for example, is performed to acquire a CTA image IMG1 from the X-ray CT device via a communication interface 111 (step S200). When the CTA image IMG1 is stored in a memory 114, the acquisition function 121 may be performed to acquire the CTA image IMG1 from the memory 114.

Subsequently, the detection function 122 is performed to analyze the continuity of the blood vessels in the brain on the basis of the CTA image IMG1 and detect branch points B of the blood vessels on the basis of an analysis result (step S202). When the detection function 122 is performed to detect arterial branch points B, an arterial branch point list LT is generated.

Subsequently, the detection function 122 is performed to detect a blood vessel diameter on the CTA image IMG1 or the cerebral artery mask image IMG2 (step S204).

For example, the detection function 122 is performed to perform a thinning process on a pixel group (a linear pixel group corresponding to a blood vessel) located between the branch points B and detect a change in a CT value of each pixel between before and after the thinning process as the blood vessel diameter. For example, the number of pixels whose CT values are greater than or equal to a threshold value in the pixel group before the thinning process is performed is denoted by X and the number of pixels whose CT values are greater than or equal to the threshold value in the pixel group after the thinning process is performed is denoted by Y. At this time, when a ratio X/Y of the number of pixels whose CT values are greater than or equal to the threshold value is larger, a larger vessel diameter (a thicker blood vessel) is detected. That is, the blood vessel having a larger number of pixels with a larger CT value has a larger diameter before the thinning process is performed than after the thinning process is performed.

Subsequently, the generation function 123 is performed to generate a blood vessel diagram of the cerebral artery on the basis of the arterial branch point list LT and the blood vessel diameter (step S206). For example, the generation function 123 is performed to generate a blood vessel diagram in which an artery having a smaller blood vessel diameter is represented by a thinner solid line and an artery having a larger blood vessel diameter is represented by a thicker solid line.

Figure 13:
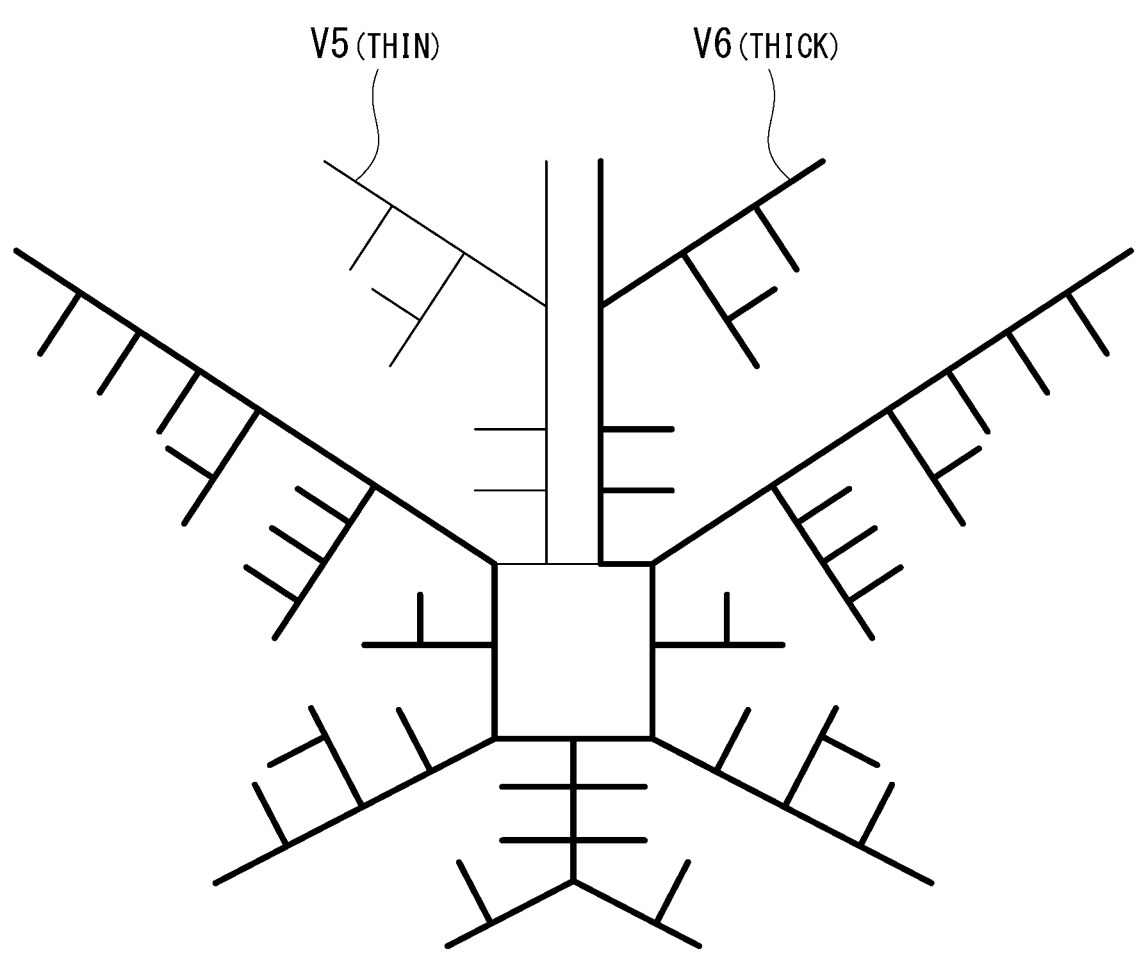
FIG. 13 is an example of a blood vessel diagram according to the second embodiment.

FIG. 13 is an example of a blood vessel diagram according to the second embodiment. For example, it is assumed that an artery V5 has a smaller blood vessel diameter than an artery V6. In this case, the generation function 123 may be performed to generate a blood vessel diagram in which the solid line indicating the artery V5 is thinner than the solid line indicating the artery V6.

Subsequently, the output control function 125 is performed to cause a display 113*a* of an output interface 113 to display the blood vessel diagram (step S208).

Subsequently, after the blood vessel diagram is displayed on the display 113*a*, the output control function 125 is performed to determine whether or not at least one or more branch points B have been selected from among the branch points B of the arterial branch point list LT associated with branches on the blood vessel diagram when the physician operates an input interface 112 (step S210). The output control function 125 may be performed to determine whether or not the physician has selected a blood vessel between the branch points B instead of the branch points B.

For example, when the physician has selected the branch point B or the blood vessel, the output control function 125 is performed to select a cross-sectional image in which the branch points B or the blood vessels, which have been selected, are drawn from among the plurality of cross-sectional images (2D-CTA images) constituting the CTA image IMG1, which is a 3D-CTA image, and cause the display 113*a* to display the cross-sectional image (step S212).

On the other hand, if the physician has not selected the branch point B or the blood vessel, the process of the present flowchart ends.

According to the above-described second embodiment, the processing circuitry 120 detects a blood vessel diameter and generates a blood vessel diagram representing a blood vessel thickness (blood vessel diameter) according to the blood vessel diameter. Thus, by schematically displaying the blood vessel diagram representing the blood vessel thickness, the user can ascertain a shape or a blood flow of the cerebral artery of a subject in a shorter period of time and in more detail.

Third Embodiment

Hereinafter, a third embodiment will be described. The third embodiment is different from the above-described first or second embodiment in that a lesion or a device placed in a subject is detected and a blood vessel diagram representing the lesion or device is generated. Hereinafter, differences from the first embodiment and the second embodiment will be mainly described and the description of parts identical to those of the first embodiment and the second embodiment will be omitted. Also, in the description of the third embodiment, parts identical to those of the first or second embodiment are denoted by the same reference signs.

Figure 14:
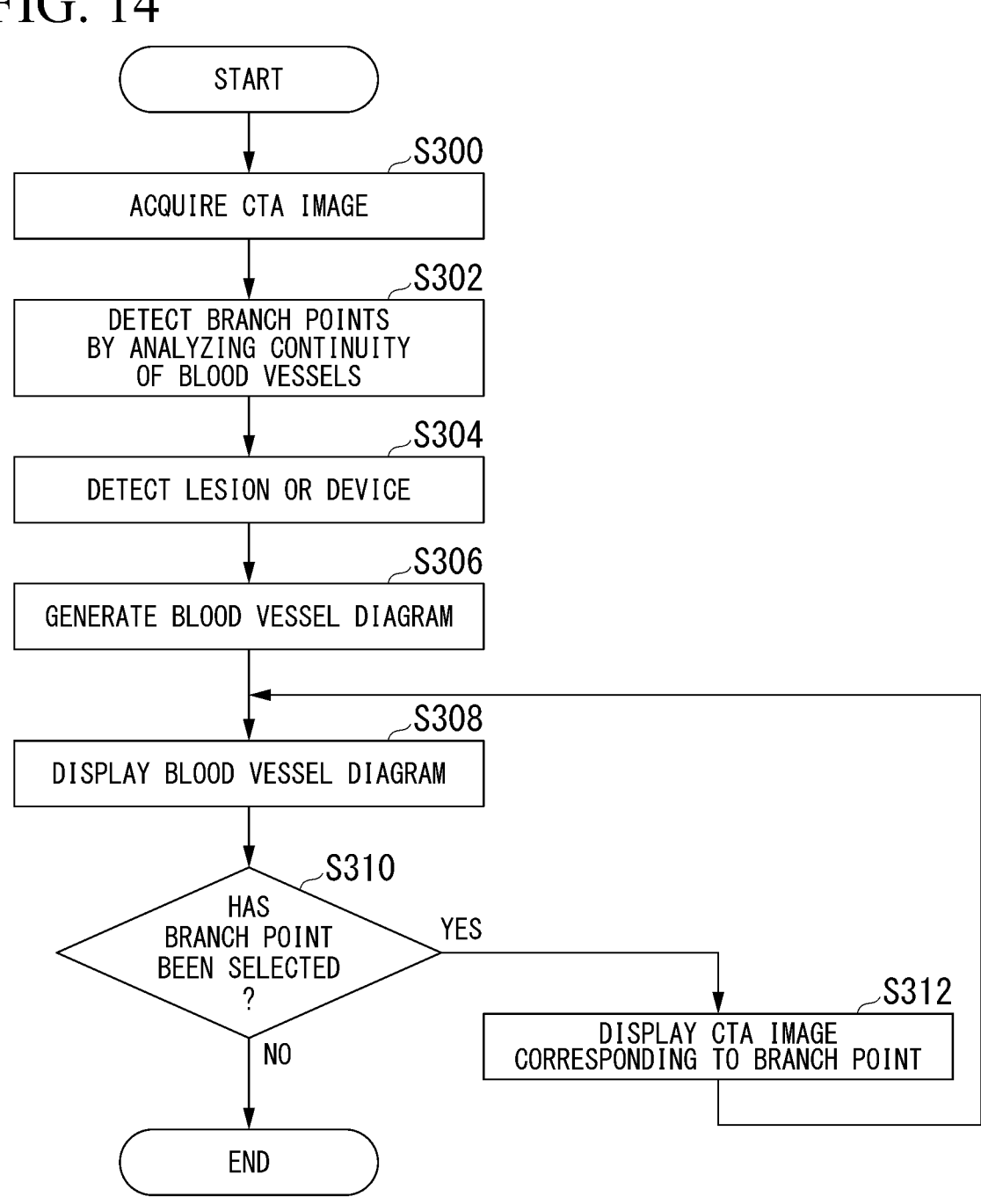
FIG. 14 is a flowchart showing a flow of a series of processing steps of processing circuitry according to a third embodiment.

FIG. 14 is a flowchart showing a flow of a series of processing steps of the processing circuitry 120 according to the third embodiment. In the present flowchart, as an example, it is assumed that a medical image diagnostic device is an X-ray CT device and a medical image is a CTA image.

First, an acquisition function 121, for example, is performed to acquire a CTA image IMG1 from the X-ray CT device via a communication interface 111 (step S300). When the CTA image IMG1 is stored in a memory 114, the acquisition function 121 may be performed to acquire the CTA image IMG1 from the memory 114.

Subsequently, a detection function 122 is performed to analyze the continuity of blood vessels of the brain on the basis of the CTA image IMG1 and detect branch points B of the blood vessels on the basis of an analysis result (step S302). When arterial branch points B are detected, the detection function 122 is performed to generate an arterial branch point list LT.

Subsequently, the detection function 122 is performed to detect a lesion or device on the CTA image IMG1 or a cerebral artery mask image IMG2 (step S304).

For example, the detection function 122 is performed to detect a blood vessel diameter on the CTA image IMG1 or the cerebral artery mask image IMG2 and detect a portion where the blood vessel diameter varies locally as the lesion or device.

Also, the detection function 122 may be performed to detect a position, type, size, and the like of the lesion or device from the CTA image IMG1 or the cerebral artery mask image IMG2 using a pre-learned classifier.

The classifier is a machine learning model trained on the basis of a training dataset. The training dataset is a dataset in which information about a correct position, type, and size of the lesion or device is labeled for the CTA image IMG1 or the cerebral artery mask image IMG2.

The classifier may be implemented, for example, by a deep neural network(s) (DNN). The classifier is not limited to the DNN and may be implemented by other models such as a support vector machine, a decision tree, a naive Bayes classifier, and a random forest. The information defined by the classifier is stored as model information in the memory 114.

When the classifier is implemented by the DNN, the model information includes, for example, coupling information indicating a method in which units included in an input layer, one or more hidden layers (intermediate layers), and an output layer constituting the DNN are coupled to each other, weight information indicating the number of coupling coefficients assigned to data input/output between the coupled units, and the like. The coupling information includes, for example, information for designating the number of units included in each layer and a type of unit to which each unit is coupled and information such as an activation function for implementing each unit and a gate provided between the units of the hidden layer. Examples of the activation function for implementing the unit may be a rectified linear unit (ReLU) function, an exponential linear units (ELU) function, a clipping function, a sigmoid function, a step function, a hyperbolic tangent function, an identity function, and the like. The gate selectively passes or weights data transmitted between units, for example, according to a value returned by the activation function (for example, 1 or 0). The coupling coefficient includes, for example, a weight applied to the output data when data is output from a unit of a certain layer to a unit of a deeper layer in the hidden layer of the neural network. Also, the coupling coefficient may include a unique bias component of each layer.

Subsequently, the generation function 123 is performed to generate a blood vessel diagram of cerebral arteries on the basis of the arterial branch point list LT and the lesion or device (step S306).

FIG. 15 is an example of a blood vessel diagram according to the third embodiment. For example, when lesions or devices have been detected, the generation function 123 is performed to generate a blood vessel diagram representing positions, types, and sizes of these lesions or devices.

Subsequently, the output control function 125 causes a display 113a of an output interface 113 to display the blood vessel diagram (step S308).

Subsequently, after the blood vessel diagram is displayed on the display 113a, the output control function 125 is performed to determine whether or not at least one or more branch points B have been selected from among the branch points B of the arterial branch point list LT associated with branches on the blood vessel diagram when the physician operates an input interface 112 (step S310). The output control function 125 may be performed to determine whether or not the physician has selected a blood vessel between the branch points B instead of the branch points B.

For example, when the physician has selected the branch point B or the blood vessel, the output control function 125 is performed to select a cross-sectional image in which the branch points B or the blood vessels, which have been selected, are drawn from among the plurality of cross-sectional images (2D-CTA images) constituting the CTA image IMG1, which is a 3D-CTA image, and cause the display 113a to display the cross-sectional image (step S312).

On the other hand, if the physician has not selected the branch point B or the blood vessel, the process of the present flowchart ends.

According to the above-described third embodiment, the processing circuitry 120 detects a lesion or a device placed within the subject and generates a blood vessel diagram representing the lesion or device. Thus, by schematically displaying the blood vessel diagram representing the lesion or device, the user can ascertain a shape or a blood flow of the cerebral artery of the subject in a shorter period of time and in more detail.

Fourth Embodiment

Hereinafter, a fourth embodiment will be described. The fourth embodiment is different from the above-described first to third embodiments in that a period of time required for a contrast medium to reach a blood vessel (hereinafter referred to as a contrast delay period of time) is calculated and a blood vessel diagram is generated on the basis of the contrast delay period of time. Hereinafter, differences from the first to third embodiments will be mainly described and the description of parts identical to those of the first to third embodiments will be omitted. Also, in the description of the fourth embodiment, parts identical to those of any one of the first to third embodiments are denoted by the same reference signs.

Figure 16:
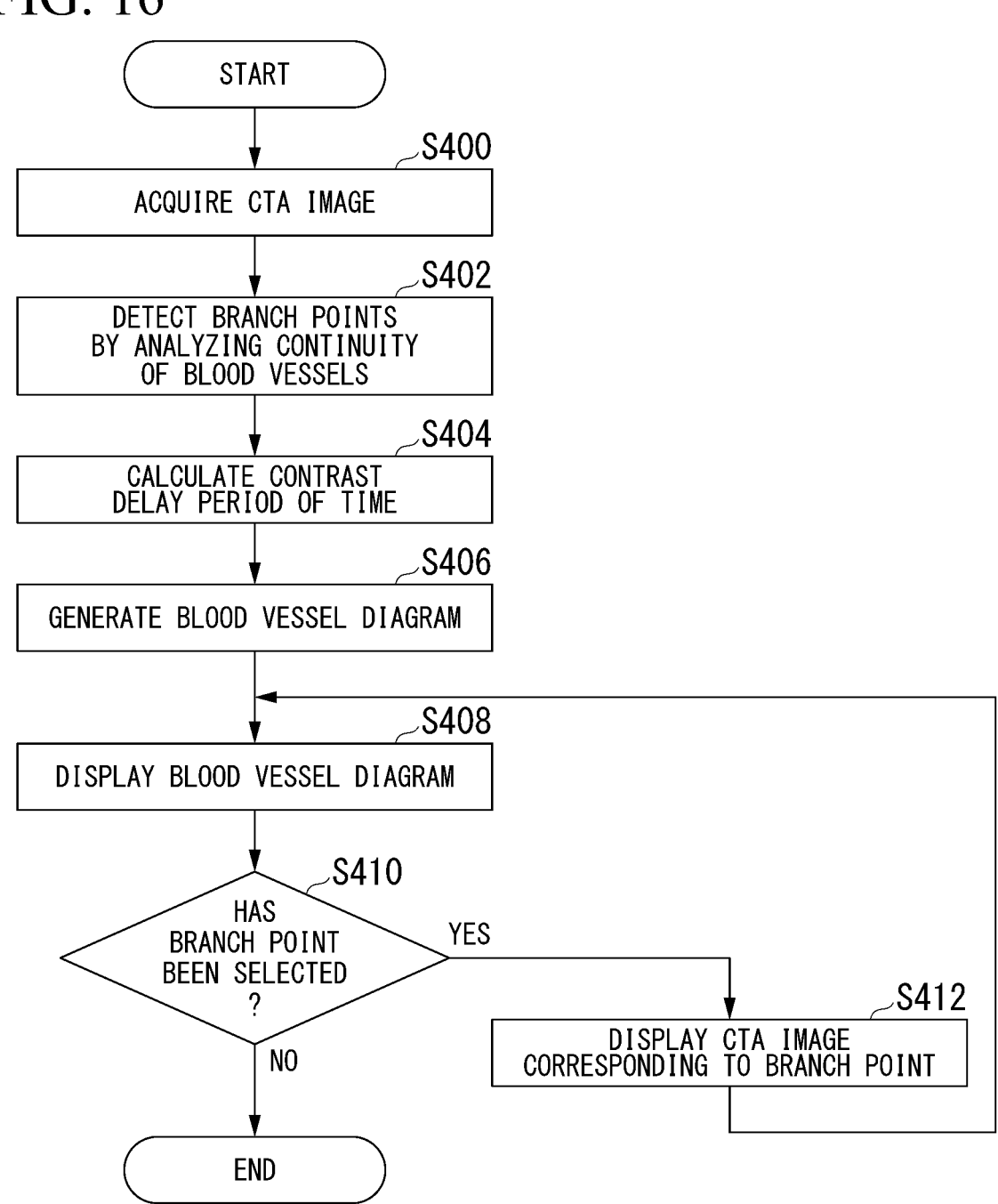
FIG. 16 is a flowchart showing a flow of a series of processing steps of processing circuitry according to the fourth embodiment.

FIG. 16 is a flowchart showing a flow of a series of processing steps of processing circuitry 120 according to the fourth embodiment. In the present flowchart, as an example, it is assumed that a medical image diagnostic device is an X-ray CT device and a medical image is a CTA image.

First, an acquisition function 121, for example, is performed to acquire a CTA image IMG1 from the X-ray CT device via a communication interface 111 (step S400). When the CTA image IMG1 is stored in a memory 114, the acquisition function 121 may be performed to acquire the CTA image IMG1 from the memory 114.

Subsequently, a detection function 122 is performed to analyze the continuity of blood vessels of the brain on the basis of the CTA image IMG1 and detect branch points B of the blood vessels on the basis of an analysis result (step S402). When arterial branch points B are detected, the detection function 122 is performed to generate an arterial branch point list LT.

Subsequently, a calculation function 124 is performed to calculate the contrast delay period of time of the blood vessel between the branch points B on the basis of the CTA image IMG1 or the cerebral artery mask image IMG2 (step S404).

For example, the calculation function 124 is performed to calculate a period of time from the time when the contrast medium has been intravenously injected to the time when a CT value of a pixel group between the branch points B has increased due to the contrast medium flowing into the blood vessel as the contrast delay period of time.

Subsequently, a generation function 123 is performed to generate a blood vessel diagram of a cerebral artery on the basis of the arterial branch point list LT and the contrast delay period of time (step S406). For example, the generation function 123 is performed to generate a blood vessel diagram in which an artery with a shorter contrast delay period of time (an artery that takes less time for the contrast medium to circulate) is indicated by a thinner solid line and an artery with a long contrast delay period of time (an artery that takes more time for the contrast medium to circulate) is indicated by a thicker solid line.

Figure 17:
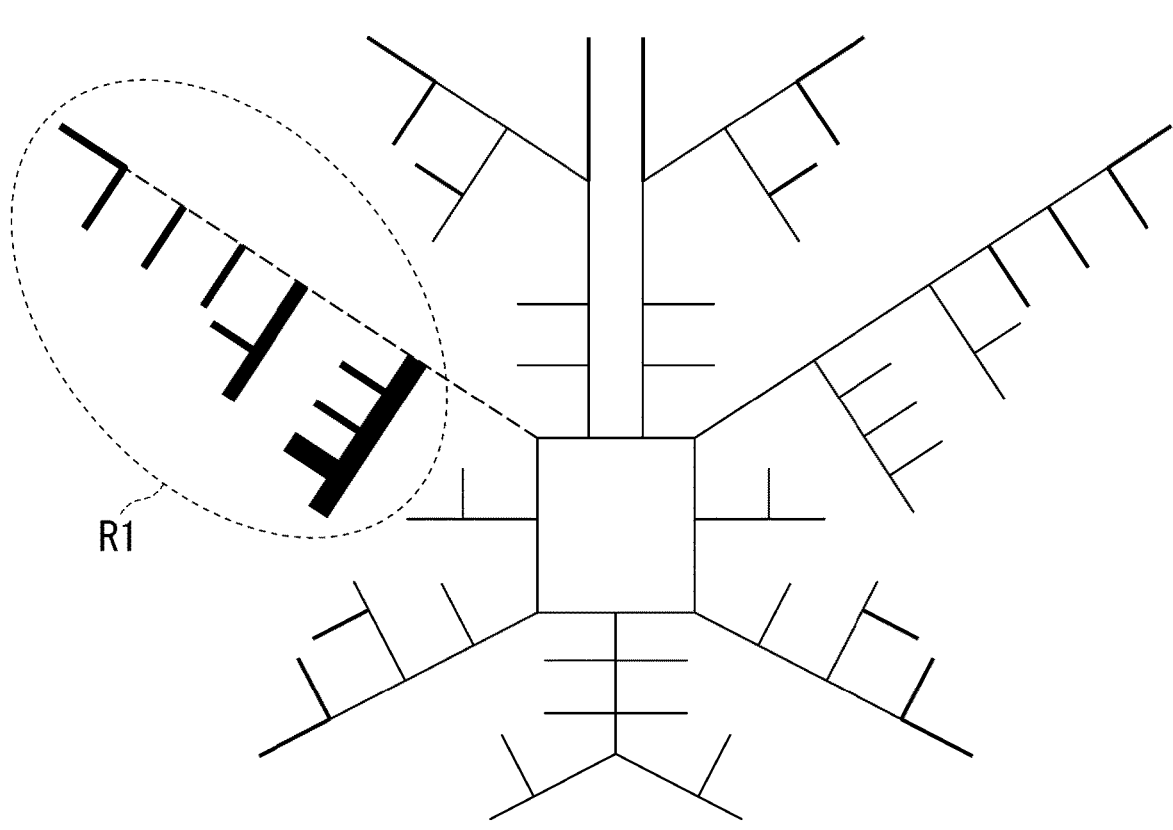
FIG. 17 is an example of a blood vessel diagram according to the fourth embodiment.

FIG. 17 is an example of a blood vessel diagram according to the fourth embodiment. In the illustrated example, the artery in a region R1 has a longer contrast delay period of time than the arteries in the other regions. In this case, the generation function 123 may be performed to generate a blood vessel diagram in which the solid line indicating the artery in the region R1 is thicker than the solid line indicating the artery in the other region. By displaying such a blood vessel diagram, for example, it is possible to make a diagnosis in which the contrast delay period of time of a peripheral part of a right middle cerebral artery is prolonged due to retrograde collateral circulation associated with infarction of the right middle cerebral artery.

Subsequently, an output control function 125 is performed to cause a display 113*a* of an output interface 113 to display the blood vessel diagram (step S408).

Subsequently, after the blood vessel diagram is displayed on the display 113*a*, the output control function 125 is performed to determine whether or not at least one or more branch points B have been selected from among the branch points B of the arterial branch point list LT associated with branches on the blood vessel diagram when the physician operates an input interface 112 (step S410). The output control function 125 may be performed to determine whether or not the physician has selected a blood vessel between the branch points B instead of the branch points B.

For example, when the physician has selected the branch point B or the blood vessel, the output control function 125 is performed to select a cross-sectional image in which the branch points B or the blood vessels, which have been selected, are drawn from among the plurality of cross-sectional images (2D-CTA images) constituting the CTA image IMG1, which is a 3D-CTA image, and cause the display 113*a* to display the cross-sectional image (step S412).

On the other hand, if the physician has not selected the branch point B or the blood vessel, the process of the present flowchart ends.

According to the above-described fourth embodiment, the processing circuitry 120 calculates a contrast delay period of time, which is a period of time required for the contrast medium to reach the blood vessel, and generates a blood vessel diagram on the basis of the contrast delay period of time. Thus, by schematically displaying a blood vessel diagram in which the display mode of the blood vessel changes according to the contrast delay period of time, the user can ascertain a shape or a blood flow of a cerebral artery of the subject in a shorter period of time and in more detail.

Fifth Embodiment

Hereinafter, a fifth embodiment will be described. The fifth embodiment is different from the first to fourth embodiments in that a density of a contrast medium distributed to a blood vessel (hereinafter referred to as a contrast density) is calculated and a blood vessel diagram is generated on the basis of the contrast density. Hereinafter, differences from the first to fourth embodiments will be mainly described and the description of parts identical to those of the first to fourth embodiments will be omitted. Also, in the description of the fifth embodiment, parts identical to those of any one of the first to fourth embodiments are denoted by the same reference signs.

Figure 18:
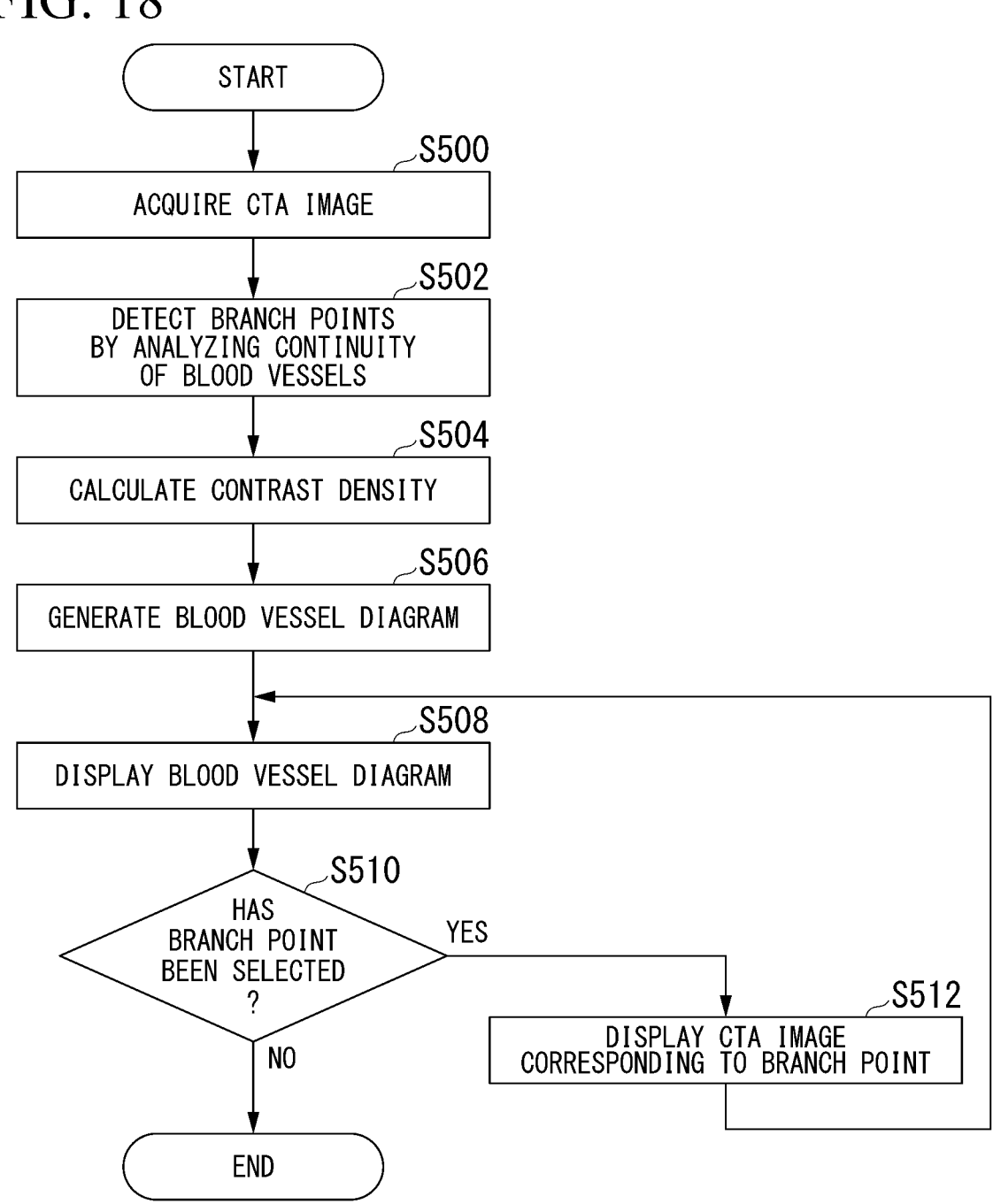
FIG. 18 is a flowchart showing a flow of a series of processing steps of processing circuitry according to a fifth embodiment.

FIG. 18 is a flowchart showing a flow of a series of processing steps of processing circuitry 120 according to the fifth embodiment. In the present flowchart, as an example, it is assumed that a medical image diagnostic device is an X-ray CT device, and a medical image is a CTA image.

First, an acquisition function 121, for example, is performed to acquire a CTA image IMG1 from the X-ray CT device via a communication interface 111 (step S500). When the CTA image IMG1 is stored in a memory 114, the acquisition function 121 may be performed to acquire the CTA image IMG1 from the memory 114.

Subsequently, a detection function 122 is performed to analyze the continuity of blood vessels of the brain on the basis of the CTA image IMG1 and detect branch points B of the blood vessels on the basis of an analysis result (step S502). When arterial branch points B are detected, the detection function 122 is performed to generate an arterial branch point list LT.

Subsequently, a calculation function 124 is performed to calculate the contrast density of the blood vessel between the branch points B on the basis of the CTA image IMG1 or a cerebral artery mask image IMG2 (step S504).

For example, the calculation function 124 is performed to calculate a time density curve of a pixel between the branch points B and calculate an area under a curve, which is the time density curve, as the contrast density.

Subsequently, a generation function 123 is performed to generate a blood vessel diagram of cerebral arteries on the basis of the arterial branch point list LT and the contrast density (step S506). For example, the generation function 123 is performed to generate a blood vessel diagram in which an artery having a higher contrast density is indicated by a thinner solid line and an artery having a lower contrast density is indicated by a thicker solid line.

Figure 19:
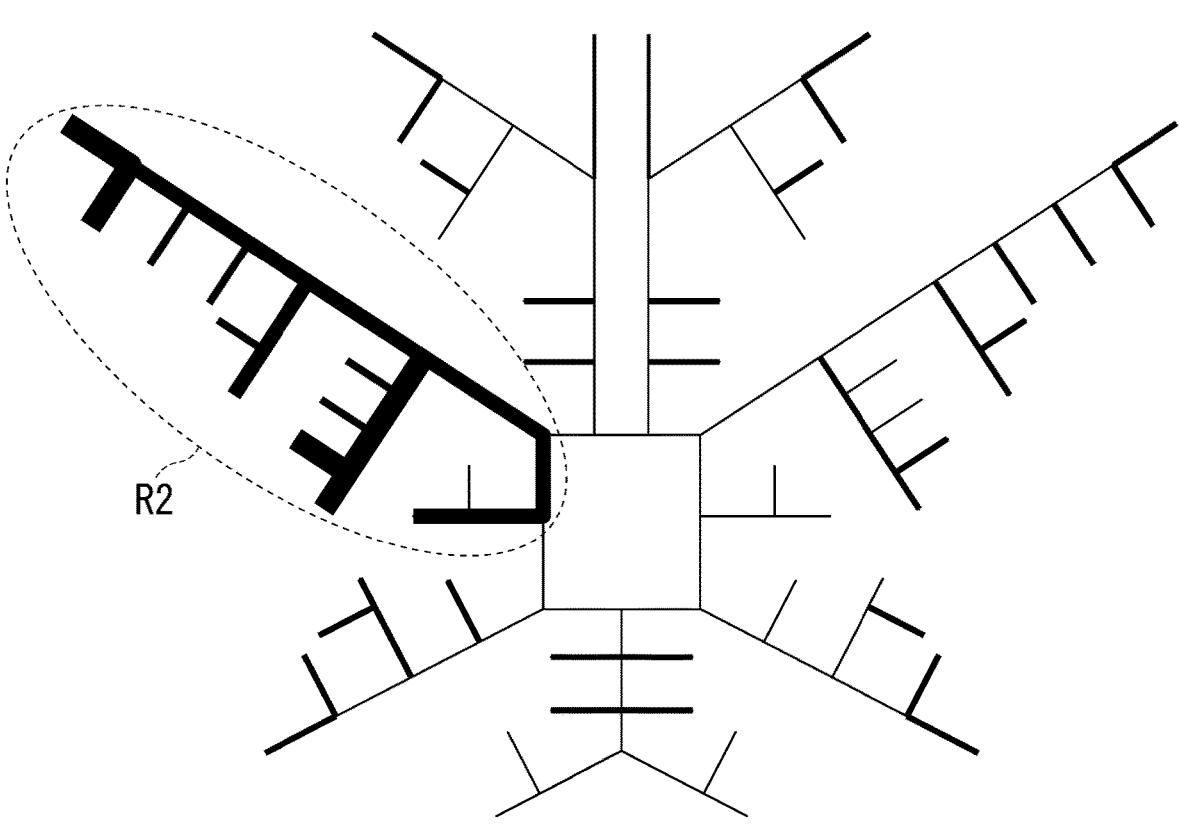
FIG. 19 is an example of a blood vessel diagram according to the fifth embodiment.

FIG. 19 is an example of a blood vessel diagram according to the fifth embodiment. In the illustrated example, an artery in a region R2 has a lower contrast density than the arteries in the other regions. In this case, the generation function 123 may be performed to generate a blood vessel diagram in which the solid line indicating the artery in the region R2 is thicker than the solid line indicating the artery in the other region. By displaying such a blood vessel diagram, for example, it is possible to make a diagnosis in which the contrast densities of a right internal carotid artery and a right middle cerebral artery are reduced due to stenosis of the right internal carotid artery.

Subsequently, an output control function 125 is performed to cause a display 113a of an output interface 113 to display a blood vessel diagram (step S508).

Subsequently, after the blood vessel diagram is displayed on the display 113a, the output control function 125 is performed to determine whether or not at least one or more branch points B have been selected from among the branch points B of the arterial branch point list LT associated with branches on the blood vessel diagram when the physician operates an input interface 112 (step S510). The output control function 125 may be performed to determine whether or not the physician has selected a blood vessel between the branch points B instead of the branch points B.

For example, when the physician has selected the branch point B or the blood vessel, the output control function 125 is performed to select a cross-sectional image in which the branch points B or the blood vessels, which have been selected, are drawn from among the plurality of cross-sectional images (2D-CTA images) constituting the CTA image IMG1, which is a 3D-CTA image, and cause the display 113a to display the cross-sectional image (step S512).

On the other hand, if the physician has not selected the branch point B or the blood vessel, the process of the present flowchart ends.

According to the above-described fifth embodiment, the processing circuitry 120 calculates a contrast density of the blood vessel and generates a blood vessel diagram on the basis of the contrast density. Thus, by schematically displaying a blood vessel diagram in which the display mode of the blood vessel changes in accordance with the contrast delay period of time, the user can ascertain a shape or a blood flow of a cerebral artery of a subject in a shorter period of time and in more detail.

Modified Example of Fifth Embodiment

Hereinafter, a modified example of the fifth embodiment will be described. In the modified example of the fifth embodiment, the display mode of the blood vessel diagram is allowed to differ in accordance with a change over time in the contrast density.

Figure 20:
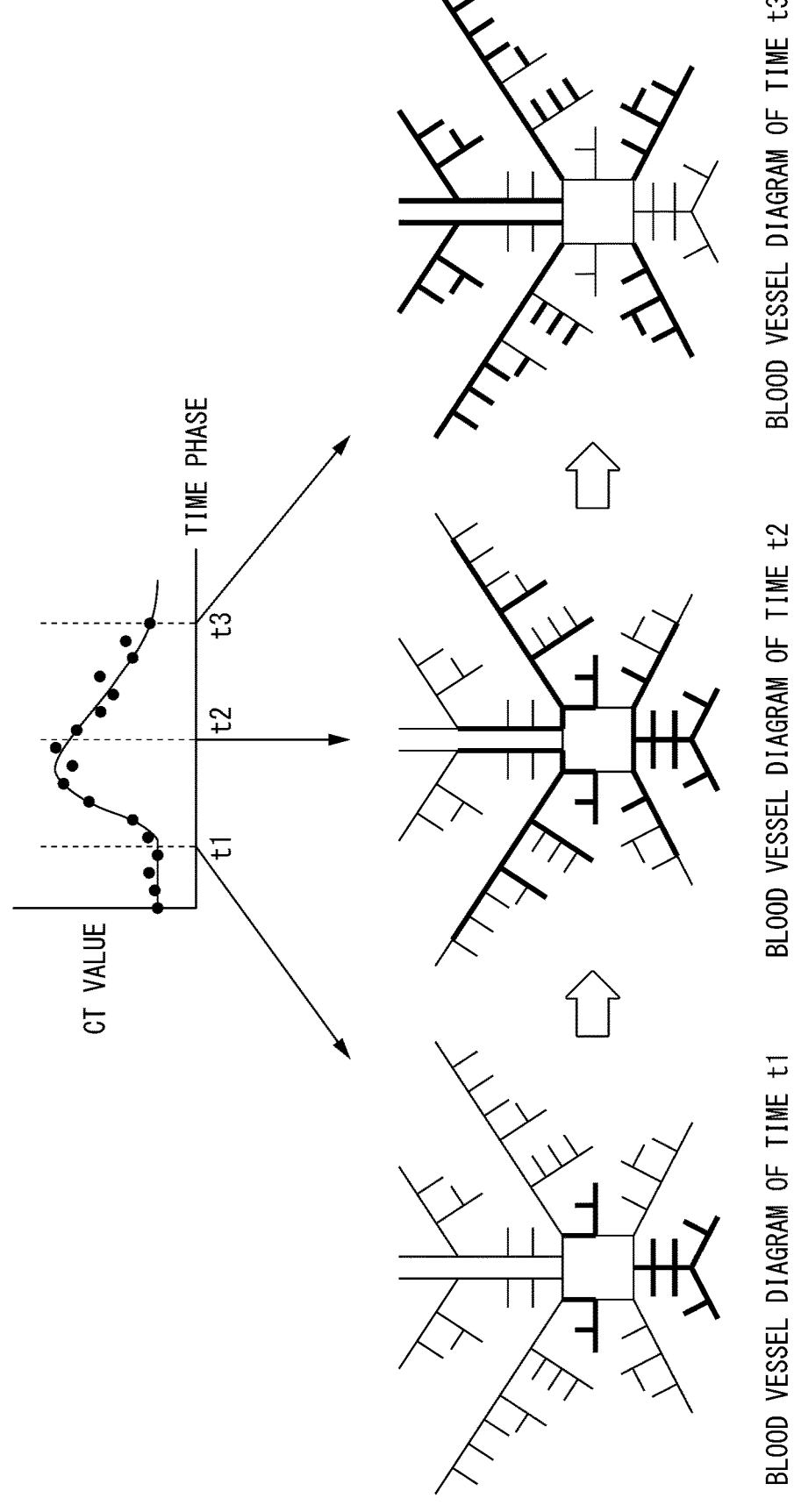
FIG. 20 is a diagram schematically showing a state in which a display mode of the blood vessel diagram changes dynamically.

FIG. 20 is a diagram schematically showing a state in which the display mode of the blood vessel diagram dynamically changes. For example, when the acquisition function 121 has been performed to acquire a 4D-CTA image, the calculation function 124 is performed to calculate the contrast density of the blood vessel between the branch points B at each time phase of the 4D-CTA image. For example, the calculation function 124 is performed to calculate a contrast density of the blood vessel between the branch points B at time t1 on the basis of a CTA image at time t1, calculate a contrast density of the blood vessel between the branch points B at time t2 on the basis of a CTA image at time t2, and calculate a contrast density of the blood vessel between the branch points B at time t3 on the basis of a CTA image at time t3.

The generation function 123 is performed to generate a blood vessel diagram at time t1 on the basis of the contrast density of the blood vessel between the branch points B at time t1, generate a blood vessel diagram at time t2 on the basis of the contrast density of the blood vessel between the branch points B at time t2, and generate a blood vessel diagram at time t3 on the basis of the contrast density of the blood vessel between the branch points B at time t3.

The output control function 125 is performed to cause the display 113a to display the blood vessel diagram at time t1, subsequently display the blood vessel diagram at time t2, and finally display the blood vessel diagram at time t3. Thus, by dynamically displaying a blood vessel diagram having a different display mode at each time, the user can ascertain a state in a period from the time when the contrast medium reaches each blood vessel to the time when the contrast medium comes out.

Sixth Embodiment

Hereinafter, a sixth embodiment will be described. The sixth embodiment is different from the first to fifth embodiments in that a blood vessel diagram of cardiac coronary arteries of a subject is generated. Hereinafter, differences from the first to fifth embodiments will be mainly described and the description of parts identical to those of the first to fifth embodiments will be omitted. Also, in the description of the sixth embodiment, parts identical to those of any one of the first to fifth embodiments are denoted by the same reference signs.

The detection function 122 of the sixth embodiment is performed to analyze the continuity of blood vessels of cardiac coronary arteries on the basis of a CTA image IMG1 and detect branch points B of the coronary arteries on the basis of an analysis result. When coronary arterial branch points B are detected, the detection function 122 is performed to generate an arterial branch point list LT.

Figure 21:
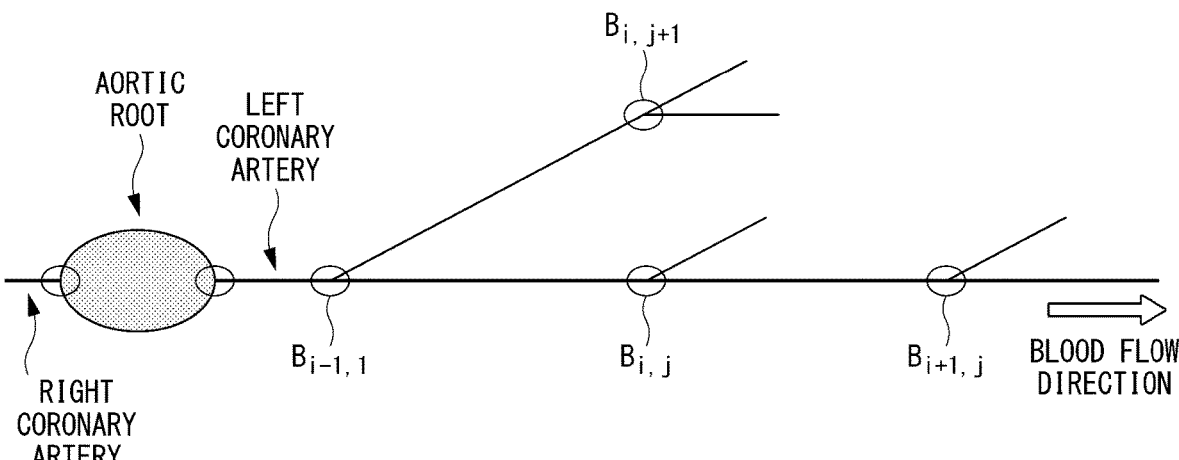
FIG. 21 is a diagram showing an example of an abstracted cardiac coronary artery.
Figure 22:
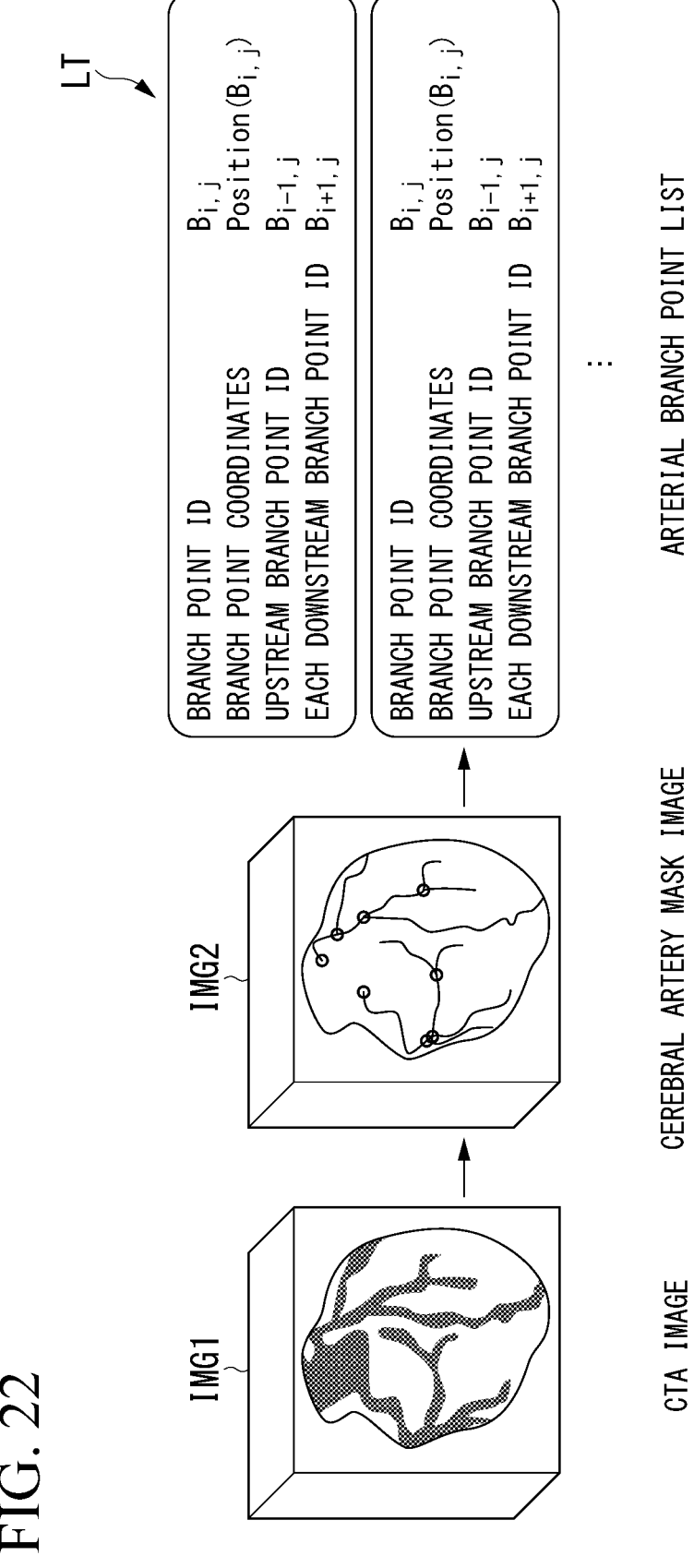
FIG. 22 schematically shows a series of flows until an arterial branch point list is generated from a CTA image of the heart.

FIG. 21 is a diagram showing an example of an abstracted cardiac coronary artery and FIG. 22 is a diagram schematically showing a series of flows until the arterial branch point list LT is generated from the CTA image IMG1 of the heart.

It is known that the cardiac coronary arteries are divided from an aortic root into a right coronary artery and a left coronary artery and have a structure that branches from each coronary artery toward the periphery (downstream). Therefore, the blood vessels branching from the coronary arteries toward the periphery are considered abstractly as shown in FIG. 21. As described above, the branch point B where the coronary artery branches may be a node and the coronary artery may be abstracted by a graph obtained by connecting the nodes with edges.

As shown in FIG. 22, the detection function 122 is performed to generate a coronary artery mask image IMG2 in which only the cardiac coronary arteries are extracted on the basis of the CTA image IMG1 of the heart. The detection function 122 is performed to detect the branch point B of the coronary artery by analyzing the structure of the blood vessel on the coronary artery mask image IMG2. Also, the detection function 122 is performed to generate the arterial branch point list LT in which these are data structurally indicating connections between the coronary artery branch points B.

The generation function 123 of the sixth embodiment is performed to generate a blood vessel diagram of the cardiac coronary arteries on the basis of the arterial branch point list LT.

For example, the generation function 123 may be performed to change (correct) a standard blood vessel diagram (a template blood vessel diagram), which is a diagram for visualizing a standard distribution structure of coronary arteries to match a connection relationship between two or more branch points B included in the arterial branch point list LT, and generate the changed standard blood vessel diagram as the blood vessel diagram.

FIG. 23 is an example of a standard blood vessel diagram of coronary arteries and FIG. 24 is a list of names of arteries drawn as a standard blood vessel diagram of coronary arteries. For example, the generation function 123 is performed to associate a standard blood vessel diagram with a branch point B included in the arterial branch point list LT at a branch from the aortic root. Furthermore, the generation function 123 is performed to associate the branch of the left coronary artery from the aortic root of the blood vessel diagram with leftmost branch point coordinates that do not have an upstream branch point in the arterial branch point list LT. Likewise, the generation function 123 is performed to associate the branch of the right coronary artery from the aortic root of the blood vessel diagram with rightmost branch point coordinates that do not have an upstream branch point in the arterial branch point list LT. The generation function 123 is performed to trace the connection with the downstream branch point with the arterial branch point list LT from the branch points associated with each other. The generation function 123 is performed to indicate the artery in the blood vessel diagram by a solid line if the connection can be traced and indicate the artery in the blood vessel diagram by a dashed line if the connection cannot be traced.

In place of or in addition to generating the blood vessel diagram using a standard blood vessel diagram and the arterial branch point list LT, the generation function 123 may be performed to generate a blood vessel diagram using only the arterial branch point list LT without using the standard blood vessel diagram. For example, the generation function 123 may be performed to generate a graph in which the branch point B is a node and the blood vessels connecting the branch points B are edges as a blood vessel diagram of coronary arteries, as shown in FIG. 21, using the arterial branch point list LT. At this time, the generation function 123 may be performed to generate the graph by applying a directed graph optimization method to reduce the number of edge intersections.

Figure 25:
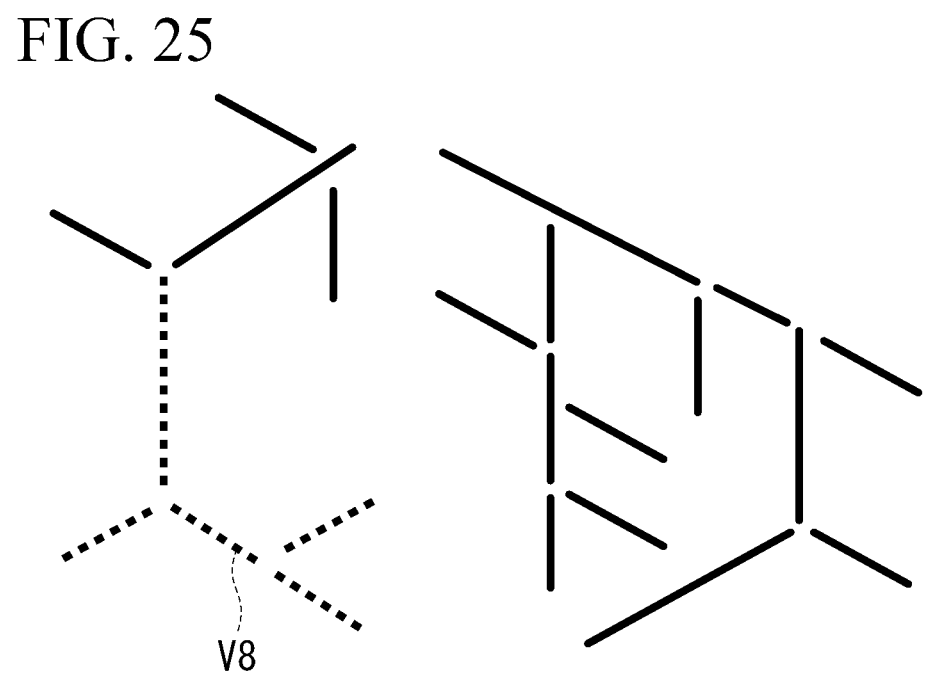

FIG. 25 is an example of a blood vessel diagram according to the fifth embodiment. In the blood vessel diagram of FIG. 25, an artery V8 is indicated by a dashed line. That is, in the blood vessel diagram of FIG. 25, a right coronary artery 2, a right coronary artery 3, an acute marginal branch, an atrioventricular branch, and a posterior descending branch (arteries having Nos. 2, 3, and 7 to 9) are not traced. If such a blood vessel diagram is displayed on display 113a, the physician can ascertain the occlusion of the right coronary artery.

According to the above-described sixth embodiment, the processing circuitry 120 acquires a CTA image IMG1, which is the CT image of the chest of the subject into whom the contrast medium has been intravenously injected. The processing circuitry 120 generates the coronary artery mask image IMG2 on the basis of the CTA image IMG1 and further detects the branch points B of the coronary arteries on a coronary artery mask image IMG2. The processing circuitry 120 generates a blood vessel diagram of the coronary arteries on the basis of the arterial branch point list LT in which the connection between the branch points B is represented in a data structure. Also, the processing circuitry 120 causes the display 113a to display the blood vessel diagram. Thus, by schematically displaying the cardiac coronary artery as the blood vessel diagram, the user (typically, the physician) can ascertain a shape or blood flow of the cardiac coronary artery of the subject in a shorter period of time.

While several embodiments of the present invention have been described above, these embodiments have been presented by way of example only, and are not intended to limit the scope of the inventions. These embodiments may be embodied in a variety of other forms. Various omissions, substitutions, and combinations may be made without departing from the spirit of the inventions. The inventions described in the accompanying claims and their equivalents are intended to cover such embodiments or modifications as would fall within the scope and spirit of the inventions.

What is claimed is:

1. A medical image processing device, comprising:
processing circuitry configured to
    acquire an angiographic image of a subject;
    detect branch points of blood vessels of the subject based on the acquired angiographic image;
    generate a blood vessel diagram, which is a diagram showing a blood vessel distribution, based on the detected branch points;
    calculate a contrast delay period of time, which is a period of time required for a contrast medium to reach the blood vessel between the detected branch points, based on the angiographic image; and
    generate the blood vessel diagram in which the blood vessel is highlighted according to the calculated contrast delay period of time.

2. The medical image processing device according to claim 1, further comprising a memory storing a standard blood vessel diagram, which is a diagram showing a standard blood vessel distribution,
    wherein the processing circuitry is further configured to generate the blood vessel diagram based on the standard blood vessel diagram and the detected branch points.

3. The medical image processing device according to claim 1, wherein the processing circuitry is further configured to cause a display to display the blood vessel diagram.

4. The medical image processing device according to claim 3, further comprising an input interface configured to be operated by a user,
    wherein the processing circuitry is further configured to cause the display to further display the angiographic image in accordance with an operation of the user input to the input interface when the blood vessel diagram is displayed on the display.

5. The medical image processing device according to claim 4, wherein the angiographic image is a three-dimensional angiographic image obtained by connecting a plurality of cross-sectional images in which a cross section of the subject is imaged, and wherein the processing circuitry is further configured to cause the display to display the cross-sectional image including one or more branch points selected by the user among the cross-sectional images of the three-dimensional angiographic image when the user has selected the one or more branch points from a plurality of branch points on the blood vessel diagram displayed on the display via the input interface.

6. The medical image processing device according to claim 1, wherein the processing circuitry is further configured to generate the blood vessel diagram based on a thickness of the blood vessel included in the angiographic image.

7. The medical image processing device according to claim 1, wherein the processing circuitry is further configured to generate the blood vessel diagram based on a shape of the blood vessel included in the angiographic image.

8. The medical image processing device according to claim 7, wherein the processing circuitry is further configured to:

detect a lesion or a device placed within the subject in the angiographic image based on the shape of the blood vessel, and generate the blood vessel diagram including the lesion or the device when the lesion or the device has been detected.

9. The medical image processing device according to claim 1, wherein the processing circuitry is further configured to generate the blood vessel diagram in which the blood vessel having a shorter contrast delay period of time is more highlighted.

10. The medical image processing device according to claim 1, wherein the processing circuitry is further configured to:

calculate a density of a contrast medium of the blood vessel between the branch points based on the angiographic image, and generate the blood vessel diagram in which the blood vessel is highlighted based on the density.

11. The medical image processing device according to claim 10, wherein the processing circuitry is further configured to generate the blood vessel diagram in which the blood vessel having a lower density is more highlighted.

12. The medical image processing device according to claim 10, wherein the processing circuitry is further configured to:

calculate a change over time in the density, and generate the blood vessel diagram whose display mode differs in accordance with the change over time in the density.

13. A medical image processing method to be executed using a computer, the medical image processing method comprising:

acquiring an angiographic image of a subject;

detecting branch points of blood vessels of the subject based on the acquired angiographic image;

generating a blood vessel diagram, which is a diagram showing a blood vessel distribution, based on the detected branch points;

calculating a contrast delay period of time, which is a period of time required for a contrast medium to reach the blood vessel between the detected branch points, based on the angiographic image; and generating the blood vessel diagram in which the blood vessel is highlighted according to the calculated contrast delay period of time.

14. A computer-readable non-transitory storage medium storing a program for causing a computer to:

acquire an angiographic image of a subject;

detect branch points of blood vessels of the subject based on the acquired angiographic image;

generate a blood vessel diagram, which is a diagram showing a blood vessel distribution, based on the branch points;

calculate a contrast delay period of time, which is a period of time required for a contrast medium to reach the blood vessel between the detected branch points, based on the angiographic image; and generate the blood vessel diagram in which the blood vessel is highlighted according to the calculated contrast delay period of time.

* * * * *